US012766144B2

(12) United States Patent
Heymach et al.

(10) Patent No.: US 12,766,144 B2
(45) Date of Patent: Oct. 20, 2026

(54) METHODS FOR TREATMENT OF CANCERS WITH EGFR ACTIVATING MUTATIONS

(71) Applicant: Board of Regents, The University of Texas System, Austin, TX (US)

(72) Inventors: John V. Heymach, Houston, TX (US); Monique Nilsson, Houston, TX (US); Jacqulyne Robichaux, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 969 days.

(21) Appl. No.: 16/980,079

(22) PCT Filed: Mar. 13, 2019

(86) PCT No.: PCT/US2019/022067

§ 371 (c)(1),
(2) Date: Sep. 11, 2020

(87) PCT Pub. No.: WO2019/178239

PCT Pub. Date: Sep. 19, 2019

(65) Prior Publication Data

US 2021/0015819 A1 Jan. 21, 2021

Related U.S. Application Data

(60) Provisional application No. 62/642,472, filed on Mar. 13, 2018.

(51) Int. Cl.

| | |
|---|---|
| ***A61K 31/519*** | (2006.01) |
| ***A61K 31/453*** | (2006.01) |
| ***A61K 45/06*** | (2006.01) |
| ***C12Q 1/686*** | (2018.01) |
| ***C12Q 1/6869*** | (2018.01) |
| ***C12Q 1/6886*** | (2018.01) |

(52) U.S. Cl.

CPC .......... *A61K 31/519* (2013.01); *A61K 31/453* (2013.01); *C12Q 1/6886* (2013.01); *A61K 45/06* (2013.01); *C12Q 1/686* (2013.01); *C12Q 1/6869* (2013.01); *C12Q 2600/156* (2013.01)

(58) Field of Classification Search

None

See application file for complete search history.

(56) References Cited

U.S. PATENT DOCUMENTS

| | | | | |
|---|---|---|---|---|
| 2010/0004232 | A1 | 1/2010 | Berdini et al. | |
| 2010/0087482 | A1 | 4/2010 | Haber et al. | |
| 2011/0033461 | A1 | 2/2011 | Ratushny et al. | |
| 2011/0301209 | A1 | 12/2011 | Zaknoen et al. | |
| 2012/0225870 | A1 | 9/2012 | Janne et al. | |
| 2013/0150342 | A1 | 6/2013 | Brain et al. | |
| 2013/0230511 | A1 | 9/2013 | Heymach et al. | |
| 2014/0121126 | A1* | 5/2014 | Bivona | G01N 33/57492 435/6.12 |
| 2014/0155397 | A1 | 6/2014 | Heymach et al. | |
| 2015/0056193 | A1* | 2/2015 | Crosby | C07K 14/70539 514/86 |
| 2015/0099737 | A1 | 4/2015 | Brain et al. | |
| 2016/0310482 | A1 | 10/2016 | Haber et al. | |
| 2016/0317538 | A1 | 11/2016 | Saha et al. | |
| 2016/0346240 | A1 | 12/2016 | Jandeleit et al. | |
| 2017/0112809 | A1 | 4/2017 | Orwar et al. | |
| 2017/0145405 | A1* | 5/2017 | Tang | A61K 38/465 |
| 2019/0134044 | A1* | 5/2019 | Shailubhai | A61P 35/00 |
| 2019/0275049 | A1* | 9/2019 | Goldberg | A61K 31/52 |

FOREIGN PATENT DOCUMENTS

| | | | |
|---|---|---|---|
| CN | 101155579 | 4/2008 | |
| CN | 102918043 | 2/2013 | |
| JP | 2009-526009 | 7/2009 | |
| JP | 2010-523536 | 7/2010 | |
| JP | 2014-141530 | 8/2014 | |
| JP | 2018-090566 | 6/2018 | |
| WO | WO 2007-090794 | 8/2007 | |
| WO | WO 2008-122779 | 10/2008 | |
| WO | WO 2015/112705 | 7/2015 | |
| WO | WO-2016201370 A1 * | 12/2016 | A61K 31/4162 |
| WO | WO-2018015448 A1 * | 1/2018 | A61K 31/517 |
| WO | WO 2018-091999 | 5/2018 | |
| WO | WO-2018156812 A1 * | 8/2018 | A61K 31/4709 |

OTHER PUBLICATIONS

Yun et al. (Proc Natl Acad Sci U S A. Feb. 12, 2008; 105(6): 2070-2075).*

Chen et al. (Journal of Thoracic Oncology vol. 12 No. 6: e65-e68, available online—Jan. 14, 2017).*

Huang et al., "Inhibition of Skp2 sensitizes lung cancer cells to paclitaxel," *Oncotargets and Therapy*, 10:439-446, 2017.

Jane et al., "Dinaciclib, a Cyclin-Dependent Kinase Inhibitor Promotes Proteasomal Degradation of Mcl-1 and Enhances ABT-737-Mediated Cell Death in Malignant Human Glioma Cell Lines," *J Pharmacol Exp Ther*, 356:354-365, 2016.

Liu et al., "PD 0332991, a selective cyclin D kinase 4/6 inhibitor, sensitizes lung cancer cells to treatment with epidermal growth factor receptor tyrosine kinase inhibitors," *Oncotarget*, 7(51):84951-84964, 2016.

PCT International Preliminary Report on Patentability issued in International Application No. PCT/US2019/022067, mailed Sep. 24, 2020.

PCT International Search Report and Written Opinion issued in International Application No. PCT/US2019/022067, mailed Aug. 6, 2019.

Stephenson et al., "Randomized phase 2 study of the cyclin-dependent kinase inhibitor dinaciclib (MK-7965) versus erlotinib in patients with non-small cell lung cancer," *Lung Cancer*, 83:219-223, 2014.

Wang et al., "Polo-like kinase 1 inhibition diminishes acquired resistance to epidermal growth factor receptor inhibition in non-small cell lung cancer with T790M mutations," *Oncotarget*, 7(30):47998-48010, 2016.

(Continued)

*Primary Examiner* — Bong-Sook Baek
(74) *Attorney, Agent, or Firm* — pH IP Law

(57) ABSTRACT

The present disclosure provides methods for treating cancer in a patient determined to have an EGFR activating mutation by administering a CDK inhibitor and/or SAC component inhibitor.

6 Claims, 24 Drawing Sheets

(56) References Cited

OTHER PUBLICATIONS

Yu et al., "Resistance to an irreversible epidermal growth factor receptor (EGFR) inhibitor in EGFR-mutant lung cancer reveals novel treatment strategies," *Cancer Res*, 67(21):10417-10427, 2007.
Kobayashi et al., "Transcriptional profiling identifies cyclin D1 as a critical downstream effector of mutant epidermal growth factor receptor signaling," *Cancer Res.*, 66(23):11389-11398, 2006.
Liu, "The mechanism study of acquired resistance of EGFR-TKIs and methods to reverse it in NSCLC," Tianjin Medical University doctoral dissertation, 2018.
Office Action issued in Chinese Application No. 201980018745.1, issued Jan. 28, 2023, and English translation thereof.
Office Action issued in Japanese Application No. 2020-548775, mailed Mar. 15, 2023, and English translation thereof.
Okamoto et al., "Overcoming erlotinib resistance in EGFR mutation-positive non-small cell lung cancer cells by targeting surviving," *Molecular Cancer Therapeutics*, 11:204-213, 2012.
Song et al., "Drug-tolerant EGFR mutant lung cancer cells rely on MCL-1 translation and are eliminated by MCL-1," *Journal of Thoracic Oncology*, 12:51582.
Kuo et al., "Targeting tumor metabolism by novel EGFR inhibitor in head and neck cancer," *Mol. Cancer Ther.*, 14(12_Suppl_2): Abstract A171, 2015.
Office Action issued in Japanese Application No. 2020-548775, mailed Dec. 14, 2023, and English translation thereof.

* cited by examiner

METHODS FOR TREATMENT OF CANCERS WITH EGFR ACTIVATING MUTATIONS

This application is a national phase application under 35 U.S.C. § 371 of International Application No. PCT/US2019/022067, filed Mar. 13, 2019, which claims the benefit of U.S. Provisional Patent Application No. 62/642,472, filed Mar. 13, 2018, each of which is incorporated herein by reference in its entirety.

This invention was made with government support under grant number CA190628 awarded by the National Institutes of Health. The government has certain rights in the invention.

BACKGROUND

1. Field

The present invention relates generally to the fields of cancer biology and medicine. More particularly, it concerns methods for treating cancer with activating EGFR mutations.

2. Description of Related Art

While EGFR mutant NSCLC patients are initially responsive to EGFR targeted therapies, resistant disease inevitably emerges. In nearly half of the resistant cases, tumors lack secondary EGFR mutations such as T790M and are refractory to 2nd and 3rd generation EGFR tyrosine kinase inhibitors (TKIs). The identification of treatment regimens with efficacy against cancers resistant to TKIs, such as T790M-negative resistance, remains a major clinical challenge.

SUMMARY

In some embodiments, the present disclosure provides a method of treating cancer in a subject comprising administering an effective amount of a cyclin dependent kinase (CDK) inhibitor and/or a spindle assembly checkpoint (SAC) component inhibitor to the subject, wherein the subject is determined to have one or more EGFR activating mutations. In some aspects, the subject is determined to have 2, 3, or 4 EGFR activating mutations. In particular aspects, the subject is human.

In some aspects, the one or more EGFR activating mutations are selected from the group consisting of L858R, an exon 19 deletion, and an exon 20 insertion. In certain aspects, the exon 19 deletion is an in-frame deletion between L747 and L749, such as an E746-A750 deletion, L747-E749 deletion, or A750P. In particular aspects, the exon 20 insertion is N771Del Ins FH. In some aspects, the EGFR mutations are G719S, G719A, S768I, E709A, R776H, or L861Q.

In certain aspects, the subject is determined to have an EGFR activating mutation by analyzing a genomic sample from the patient. In some aspects, the genomic sample is isolated from saliva, blood, urine, normal tissue, or tumor tissue. In some aspects, the presence of an EGFR activating mutation is determined by nucleic acid sequencing or PCR analyses.

In some aspects, the CDK inhibitor is further defined as a CDK2 inhibitor, CDK5 inhibitor, CDK1 inhibitor, or CDK9 inhibitor. In certain aspects, the CDK inhibitor is dinaciclib (SCH727965), alvocidib (flavopiridol), roscovitine (seliciclib, CYC202), SNS-032 (BMS-387032), LY2857785, ADZ5438, BMS-265246, NU6027, LDC000067, wogonin, or RO-3306. In certain aspects, the CDK inhibitor is MSC2530818, senexin A, LDC4297 (LDC044297), PHA-793887, BS-181 HCl, PHA-767491, THZ1 2HCl, or XL413. In some aspects, the CDK inhibitor is dinaciclib or alvocidib. In certain aspects, the CDK inhibitor is not a CDK4 inhibitor and/or CDK6 inhibitor. In particular aspects, the CDK inhibitor is not palociclib (PD0332991), abemaciclib (LY2835219), or ribociclob.

In certain aspects, the SAC component inhibitor is further defined as a polo-like kinase 1 (PLK1) inhibitor, Aurora kinase inhibitor, survivin, and/or KSP inhibitor. In some aspects, the PLK1 inhibitor is BI 2536, volasertib, GSK461364, ON-01910, GW 843682X, or HMN-214. In some aspects, the PLK1 inhibitor is volasertib or ON-01910. In other aspects, the SAC inhibitor is not a PLK1 inhibitor. In some aspects, the Aurora kinase inhibitor is a Pan-Aurora inhibitor, Aurora A/B inhibitor, or an Aurora A inhibitor. In certain aspects, the Aurora kinase inhibitor is AMG 900, alisertib, PF-03814735, Tozasertib, MLN8054, or SNS-314 Mesylate. In some aspects, the Aurora kinase inhibitor is AMG-900 or alisertib. In some aspects, the KSP inhibitor is ispinesib or SB743921. In some aspects, the survivin inhibitor is YM155.

In some aspects, the treatment results in accumulation of cells in the G2/M phase, enlarged nuclear size, and/or polyploidy.

In certain aspects, the cancer is resistant to one or more tyrosine kinase inhibitors (TKIs). In some aspects, the one or more TKIs are selected from the group consisting of osimertinib, erlotinib, gefitinib, afatinib, poziotinib, dacomitinib, and CO-1686. In some aspects, the cancer has acquired broad spectrum drug resistance. In some aspects, the cancer is resistant to pemetrexed, irinotecan, vinblastine, and/or gemcitabine. In certain aspects, the cancer has acquired mutations for poziotinib and/or other TKIs. In some aspects, the acquired mutation for poziotinib comprises an EGFR exon 20 insertion. In some aspects, the cancer has undergone epithelial to mesenchymal transition (EMT). In some aspects, EMT is demonstrated by decreased E-cadherin expression, increased expression of vimentin and/or Axl, and/or an increased invasive phenotype.

In additional aspects, the subject is further determined to comprise a secondary mutation. In some aspects, the secondary mutation is a T790M resistance mutation. In other aspects, the subject is determined to not have a secondary mutation. In some aspects, the subject is determined to not have a T790M resistance mutation.

In further aspects, the method further comprises administering at least one additional anti-cancer therapy. In some aspects, the at least one additional anti-cancer therapy is chemotherapy, radiotherapy, gene therapy, surgery, hormonal therapy, anti-angiogenic therapy or immunotherapy. In some aspects, the at least one additional anti-cancer therapy is a TM and/or chemotherapy. In particular aspects, the TKI is osimertinib, erlotinib, gefitinib, afatinib, dacomitinib, or CO-1686. In certain aspects, the chemotherapy is pemetrexed, irinotecan, vinblastine, or gemcitabine.

In some aspects, the CDK inhibitor, SAC component inhibitor, and/or anti-cancer therapy are administered intravenously, subcutaneously, intraosseously, orally, transdermally, in sustained release, in controlled release, in delayed release, as a suppository, or sublingually. In some aspects, administering the CDK inhibitor, SAC component inhibitor, and/or anti-cancer therapy comprises local, regional or systemic administration. In certain aspects, the CDK inhibitor, SAC component inhibitor, and/or anti-cancer therapy are administered two or more times.

In some aspects, the cancer is oral cancer, oropharyngeal cancer, nasopharyngeal cancer, respiratory cancer, urogenital cancer, gastrointestinal cancer, central or peripheral nervous system tissue cancer, an endocrine or neuroendocrine cancer or hematopoietic cancer, glioma, sarcoma, carcinoma, lymphoma, melanoma, fibroma, meningioma, brain cancer, oropharyngeal cancer, nasopharyngeal cancer, renal cancer, biliary cancer, pheochromocytoma, pancreatic islet cell cancer, Li-Fraumeni tumors, thyroid cancer, parathyroid cancer, pituitary tumors, adrenal gland tumors, osteogenic sarcoma tumors, multiple neuroendocrine type I and type II tumors, breast cancer, lung cancer, head and neck cancer, prostate cancer, esophageal cancer, tracheal cancer, liver cancer, bladder cancer, stomach cancer, pancreatic cancer, ovarian cancer, uterine cancer, cervical cancer, testicular cancer, colon cancer, rectal cancer or skin cancer. In particular aspects, the cancer is non-small cell lung cancer.

In another embodiment, there is provided a pharmaceutical composition comprising a CDK inhibitor and/or SAC component inhibitor for use in a subject determined to have one or more EGFR activating mutations.

In some aspects, the one or more EGFR activating mutations are selected from the group consisting of L858R, an exon 19 deletion, and an exon 20 insertion. In certain aspects, the exon 19 deletion is an in-frame deletion between L747 and L749. In particular aspects, the exon 20 insertion is N771Del Ins FH.

In certain aspects, the subject was determined to have an EGFR activating mutation by analyzing a genomic sample from the patient. In some aspects, the genomic sample is isolated from saliva, blood, urine, normal tissue, or tumor tissue. In some aspects, the presence of an EGFR activating mutation is determined by nucleic acid sequencing or PCR analyses.

In some aspects, the CDK inhibitor is further defined as a CDK2 inhibitor, CDK5 inhibitor, CDK1 inhibitor, or CDK 9 inhibitor. In certain aspects, the CDK inhibitor is dinaciclib (SCH727965), alvocidib (flavopiridol), roscovitine (seliciclib, CYC202), SNS-032 (BMS-387032), LY2857785, ADZ5438, BMS-265246, NU6027, LDC000067, wogonin, or RO-3306. In certain aspects, the CDK inhibitor is MSC2530818, senexin A, LDC4297 (LDC044297), PHA-793887, BS-181 HCl, PHA-767491, THZ1 2HCl, or XL413. In some aspects, the CDK inhibitor is dinaciclib or alvocidib. In certain aspects, the CDK inhibitor is not a CDK4 inhibitor and/or CDK6 inhibitor. In particular aspects, the CDK inhibitor is not palociclib (PD0332991), abemaciclib (LY2835219), or ribociclob.

In certain aspects, the SAC component inhibitor is further defined as a polo-like kinase 1 (PLK1) inhibitor, Aurora kinase inhibitor, survivin, and/or KSP inhibitor. In some aspect, the PLK1 inhibitor is BI 2536, volasertib, GSK461364, ON-01910, GW 843682X, or HMN-214. In some aspects, the PLK1 inhibitor is volasertib or ON-01910. In other aspects, the SAC inhibitor is not a PLK1 inhibitor. In some aspects, the Aurora kinase inhibitor is a Pan-Aurora inhibitor, Aurora A/B inhibitor, or an Aurora A inhibitor. In certain aspects, the Aurora kinase inhibitor is AMG 900, alisertib, PF-03814735, Tozasertib, MLN8054, or SNS-314 Mesylate. In some aspects, the Aurora kinase inhibitor is AMG-900 or alisertib. In some aspects, the KSP inhibitor is ispinesib or SB743921. In some aspects, the survivin inhibitor is YM155.

In certain aspects, the cancer is resistant to one or more tyrosine kinase inhibitors (TKIs). In some aspects, the one or more TKIs are selected from the group consisting of osimertinib, erlotinib, gefitinib, afatinib, poziotinib, dacomitinib, and CO-1686. In some aspects, the cancer has acquired broad spectrum drug resistance. In some aspects, the cancer is resistant to pemetrexed, irinotecan, vinblastine, and/or gemcitabine. In certain aspects, the cancer has acquired mutations for poziotinib and other TKIs. In some aspects, the acquired mutation for poziotinib comprises an EGFR exon 20 insertion. In some aspects, the cancer has undergone epithelial to mesenchymal transition (EMT). In some aspects, EMT is demonstrated by decreased E-cadherin expression, increased expression of vimentin and/or Axl, and/or an increased invasive phenotype.

In additional aspects, the subject is further determined to comprise a secondary mutation. In some aspects, the secondary mutation is a T790M resistance mutation, C797S resistance mutation or L792H resistance mutation. In other aspects, the subject is determined to not have a secondary mutation. In some aspects, the subject is determined to not have a T790M resistance mutation.

In further aspects, the composition further comprises at least one additional anti-cancer therapy. In some aspects, the at least one additional anti-cancer therapy is chemotherapy, radiotherapy, gene therapy, surgery, hormonal therapy, anti-angiogenic therapy or immunotherapy. In some aspects, the at least one additional anti-cancer therapy is a TKI and/or chemotherapy. In particular aspects, the TKI is osimertinib, erlotinib, gefitinib, afatinib, dacomitinib, or CO-1686. In certain aspects, the chemotherapy is pemetrexed, irinotecan, vinblastine, or gemcitabine.

In some aspects, the cancer is oral cancer, oropharyngeal cancer, nasopharyngeal cancer, respiratory cancer, urogenital cancer, gastrointestinal cancer, central or peripheral nervous system tissue cancer, an endocrine or neuroendocrine cancer or hematopoietic cancer, glioma, sarcoma, carcinoma, lymphoma, melanoma, fibroma, meningioma, brain cancer, oropharyngeal cancer, nasopharyngeal cancer, renal cancer, biliary cancer, pheochromocytoma, pancreatic islet cell cancer, Li-Fraumeni tumors, thyroid cancer, parathyroid cancer, pituitary tumors, adrenal gland tumors, osteogenic sarcoma tumors, multiple neuroendocrine type I and type II tumors, breast cancer, lung cancer, head and neck cancer, prostate cancer, esophageal cancer, tracheal cancer, liver cancer, bladder cancer, stomach cancer, pancreatic cancer, ovarian cancer, uterine cancer, cervical cancer, testicular cancer, colon cancer, rectal cancer or skin cancer. In particular aspects, the cancer is non-small cell lung cancer.

In another embodiment, there is provided a method of predicting a response to a CDK inhibitor and/or SAC component inhibitor alone or in combination with a second anti-cancer therapy in a subject having a cancer comprising detecting an EGFR activating mutation in a genomic sample obtained from said patient, wherein if the sample is positive for the presence of the EGFR activating mutation, then the patient is predicted to have a favorable response to the CDK inhibitor and/or SAC component inhibitor alone or in combination with an anti-cancer therapy.

In some aspects, a favorable response to CDK inhibitor and/or SAC component inhibitor alone or in combination with an anti-cancer therapy comprises reduction in tumor size or burden, blocking of tumor growth, reduction in tumor-associated pain, reduction in cancer associated pathology, reduction in cancer associated symptoms, cancer non-progression, increased disease free interval, increased time to progression, induction of remission, reduction of metastasis, or increased patient survival.

In some aspects, the one or more EGFR activating mutations are selected from the group consisting of L858R, an exon 19 deletion, and an exon 20 insertion. In certain aspects, the exon 19 deletion is an in-frame deletion between L747 and L749. In particular aspects, the exon 20 insertion is N771Del Ins FH.

In certain aspects, the subject was determined to have an EGFR activating mutation by analyzing a genomic sample from the patient. In some aspects, the genomic sample is isolated from saliva, blood, urine, normal tissue, or tumor tissue. In some aspects, the presence of an EGFR activating mutation is determined by nucleic acid sequencing or PCR analyses.

In some aspects, the CDK inhibitor is further defined as a CDK2 inhibitor, CDK5 inhibitor, CDK1 inhibitor, or CDK 9 inhibitor. In certain aspects, the CDK inhibitor is dinaciclib (SCH727965), alvocidib (flavopiridol), roscovitine (seliciclib, CYC202), SNS-032 (BMS-387032), LY2857785, ADZ5438, BMS-265246, NU6027, LDC000067, wogonin, or RO-3306. In certain aspects, the CDK inhibitor is MSC2530818, senexin A, LDC4297 (LDC044297), PHA-793887, BS-181 HCl, PHA-767491, THZ1 2HCl, or XL413. In some aspects, the CDK inhibitor is dinaciclib or alvocidib. In certain aspects, the CDK inhibitor is not a CDK4 inhibitor and/or CDK6 inhibitor. In particular aspects, the CDK inhibitor is not palociclib (PD0332991), abemaciclib (LY2835219), or ribociclob.

In certain aspects, the SAC component inhibitor is further defined as a polo-like kinase 1 (PLK1) inhibitor, Aurora kinase inhibitor, survivin, and/or KSP inhibitor. In some aspect, the PLK1 inhibitor is BI 2536, volasertib, GSK461364, ON-01910, GW 843682X, or HMN-214. In some aspects, the PLK1 inhibitor is volasertib or ON-01910. In other aspects, the SAC inhibitor is not a PLK1 inhibitor. In some aspects, the Aurora kinase inhibitor is a Pan-Aurora inhibitor, Aurora A/B inhibitor, or an Aurora A inhibitor. In certain aspects, the Aurora kinase inhibitor is AMG 900, alisertib, PF-03814735, Tozasertib, MLN8054, or SNS-314 Mesylate. In some aspects, the Aurora kinase inhibitor is AMG-900 or alisertib. In some aspects, the KSP inhibitor is ispinesib or SB743921. In some aspects, the survivin inhibitor is YM155.

In certain aspects, the cancer is resistant to one or more tyrosine kinase inhibitors (TKIs). In some aspects, the one or more TKIs are selected from the group consisting of osimertinib, erlotinib, gefitinib, afatinib, poziotinib, dacomitinib, and CO-1686. In some aspects, the cancer has acquired broad spectrum drug resistance. In some aspects, the cancer is resistant to pemetrexed, irinotecan, vinblastine, and/or gemcitabine. In certain aspects, the cancer has acquired mutations for poziotinib and other TKIs. In some aspects, the acquired mutation for poziotinib comprises an EGFR exon 20 insertion. In some aspects, the cancer has undergone epithelial to mesenchymal transition (EMT). In some aspects, EMT is demonstrated by decreased E-cadherin expression, increased expression of vimentin and/or Axl, and/or an increased invasive phenotype.

In additional aspects, the subject is further determined to comprise a secondary mutation. In some aspects, the secondary mutation is a T790M resistance mutation. In other aspects, the subject is determined to not have a secondary mutation. In some aspects, the subject is determined to not have a T790M resistance mutation.

In additional aspects, the method further comprises administering CDK inhibitor and/or SAC component inhibitor alone or in combination with a second anti-cancer therapy to said patient predicted to have a favorable response. In some aspects, the at least one additional anti-cancer therapy is chemotherapy, radiotherapy, gene therapy, surgery, hormonal therapy, anti-angiogenic therapy or immunotherapy. In some aspects, the at least one additional anti-cancer therapy is a TKI and/or chemotherapy. In particular aspects, the TKI is osimertinib, erlotinib, gefitinib, afatinib, dacomitinib, or CO-1686. In certain aspects, the chemotherapy is pemetrexed, irinotecan, vinblastine, or gemcitabine.

In some aspects, the CDK inhibitor, SAC component inhibitor, and/or anti-cancer therapy are administered intravenously, subcutaneously, intraosseously, orally, transdermally, in sustained release, in controlled release, in delayed release, as a suppository, or sublingually. In some aspects, administering the CDK inhibitor, SAC component inhibitor, and/or anti-cancer therapy comprises local, regional or systemic administration. In certain aspects, the CDK inhibitor, SAC component inhibitor, and/or anti-cancer therapy are administered two or more times.

In some aspects, the cancer is oral cancer, oropharyngeal cancer, nasopharyngeal cancer, respiratory cancer, urogenital cancer, gastrointestinal cancer, central or peripheral nervous system tissue cancer, an endocrine or neuroendocrine cancer or hematopoietic cancer, glioma, sarcoma, carcinoma, lymphoma, melanoma, fibroma, meningioma, brain cancer, oropharyngeal cancer, nasopharyngeal cancer, renal cancer, biliary cancer, pheochromocytoma, pancreatic islet cell cancer, Li-Fraumeni tumors, thyroid cancer, parathyroid cancer, pituitary tumors, adrenal gland tumors, osteogenic sarcoma tumors, multiple neuroendocrine type I and type II tumors, breast cancer, lung cancer, head and neck cancer, prostate cancer, esophageal cancer, tracheal cancer, liver cancer, bladder cancer, stomach cancer, pancreatic cancer, ovarian cancer, uterine cancer, cervical cancer, testicular cancer, colon cancer, rectal cancer or skin cancer. In particular aspects, the cancer is non-small cell lung cancer.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
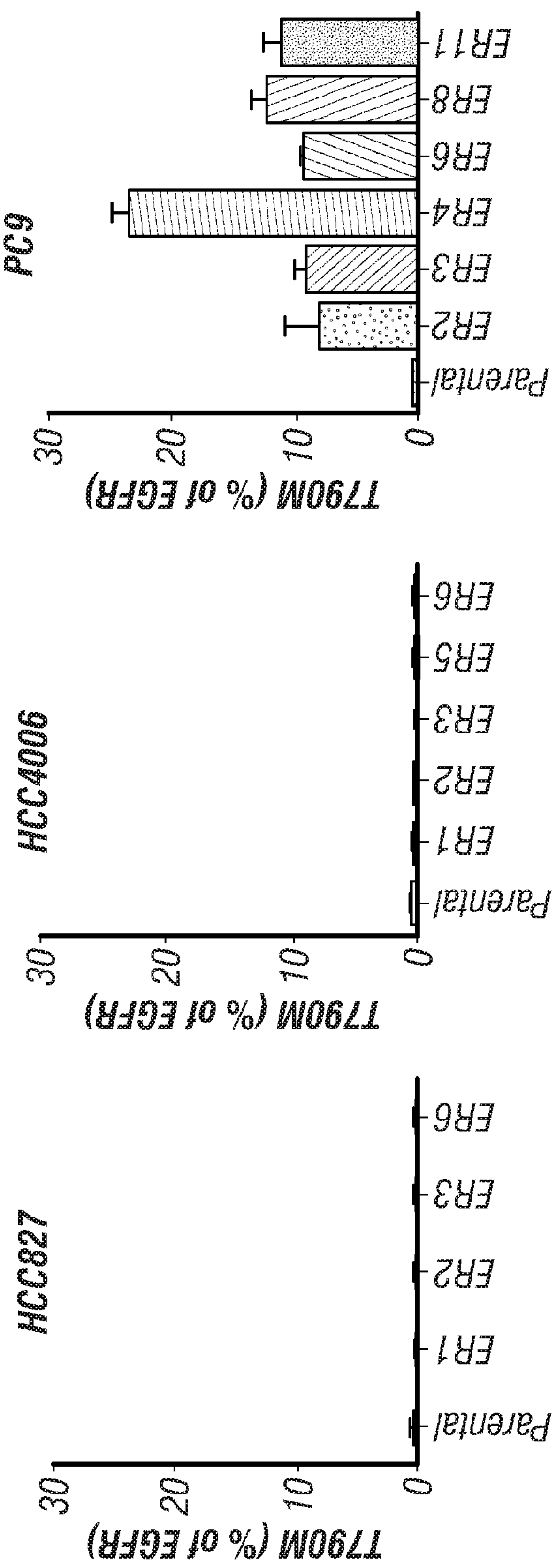
FIG. 1: HCC827 and HCC4006 ER cells were negative for T790M secondary EGFR mutations. HCC827 ER cells are resistant to multiple EGFR inhibitors including erlotinib, gefitinib, afatinib, CO-1686, and osimertinib.
Figure 1:
Figure 2A:
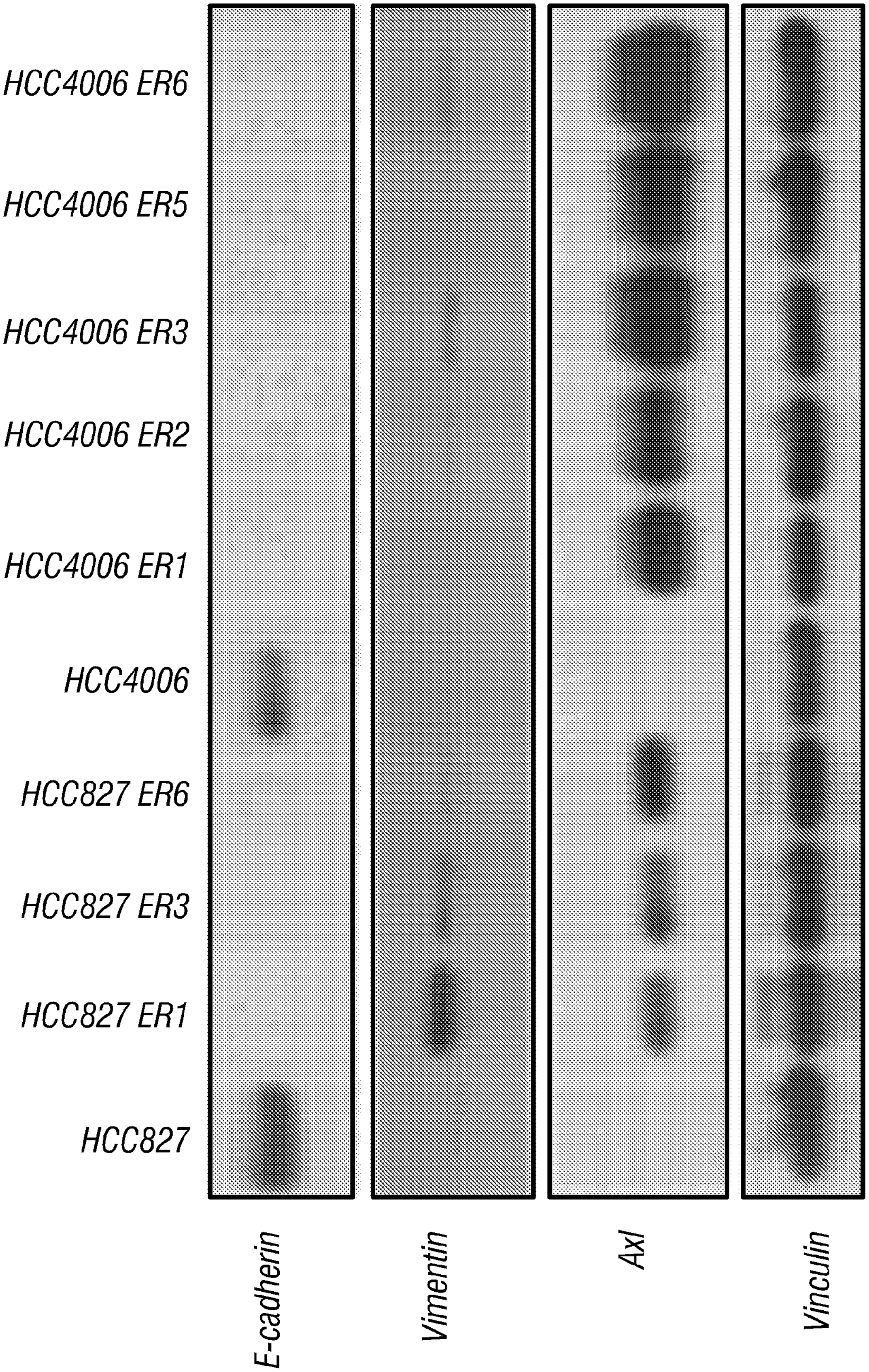
FIGS. 2A-2D: (A) HCC827 erlotinib resistant (ER) and HCC4006 ER variants have undergone an epithelial to mesenchymal transition (EMT) as demonstrated by a loss of E-cadherin and increased expression of vimentin and Axl. (B) HCC827 ER and HCC4006 ER cells display a significantly increased invasive capacity as determined by Boyden chamber assay. (C) RPPA proteomic analysis revealed alteration in EMT-related proteins and signal transduction pathways in ER cells compared to parental NSCLC cell lines. (D) RPPA proteomic profiling reveals heterogeneity between ER clones derived from the same parental cell lines.
Figure 2B:
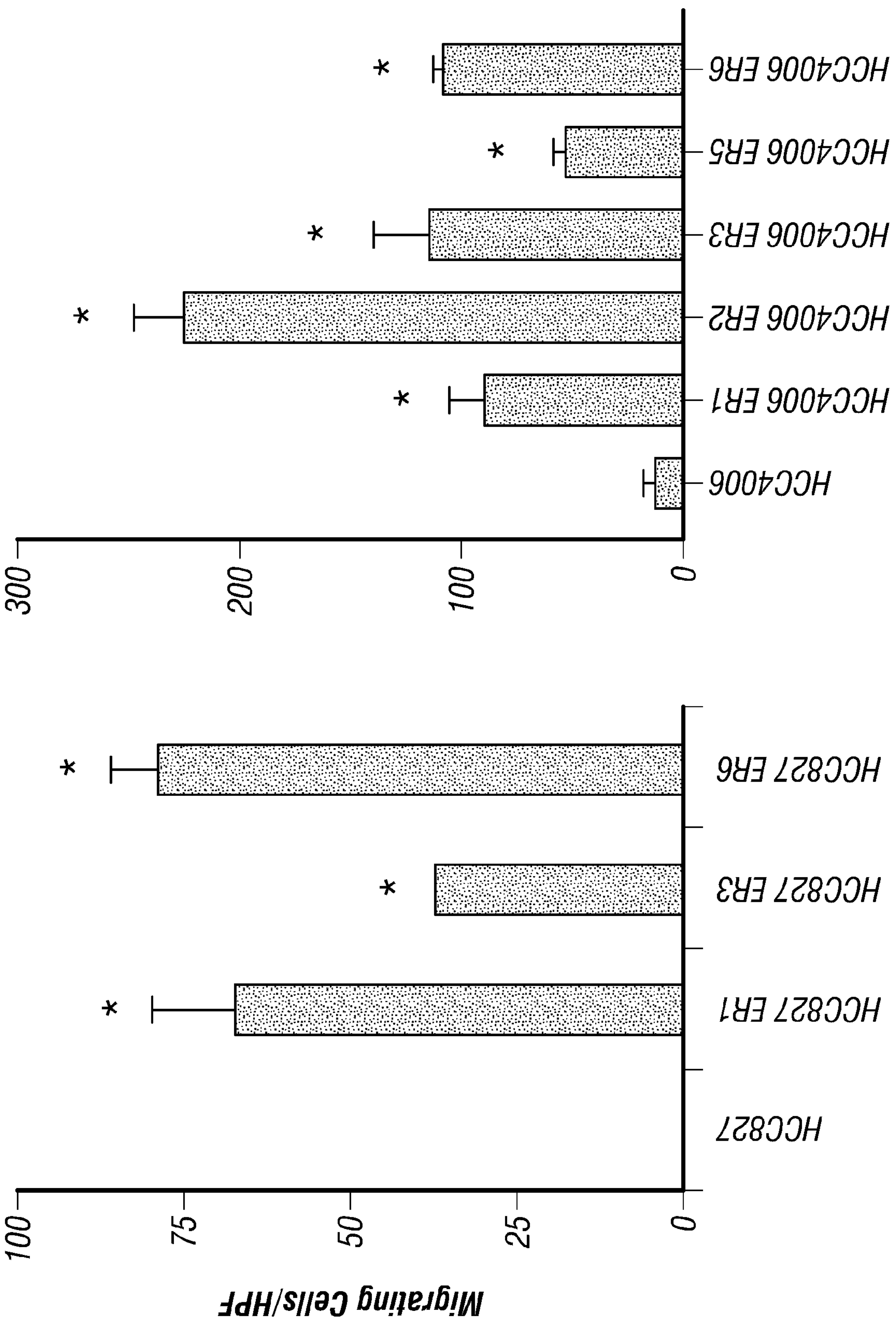
Figure 2C:
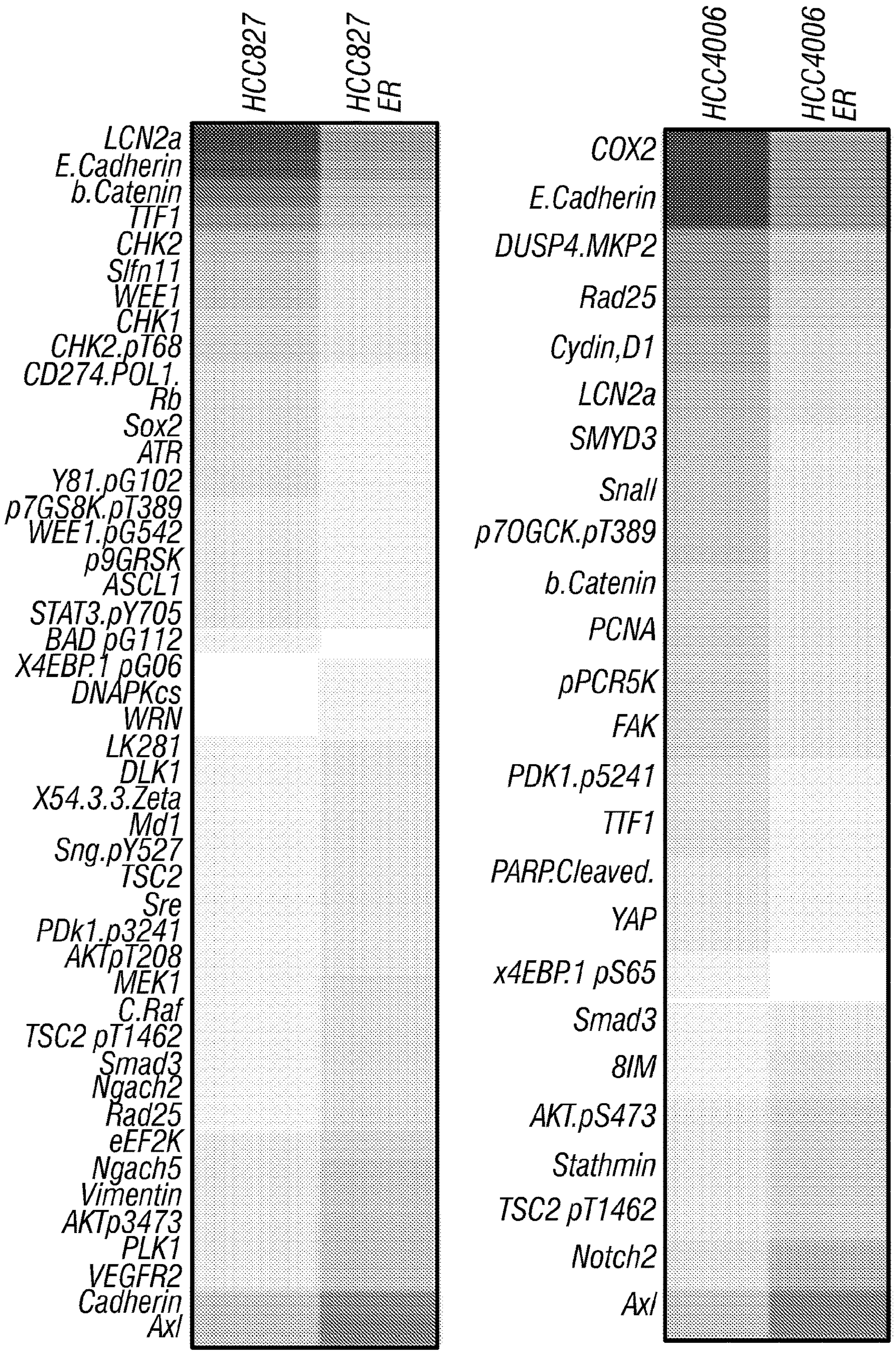
Figure 2D:
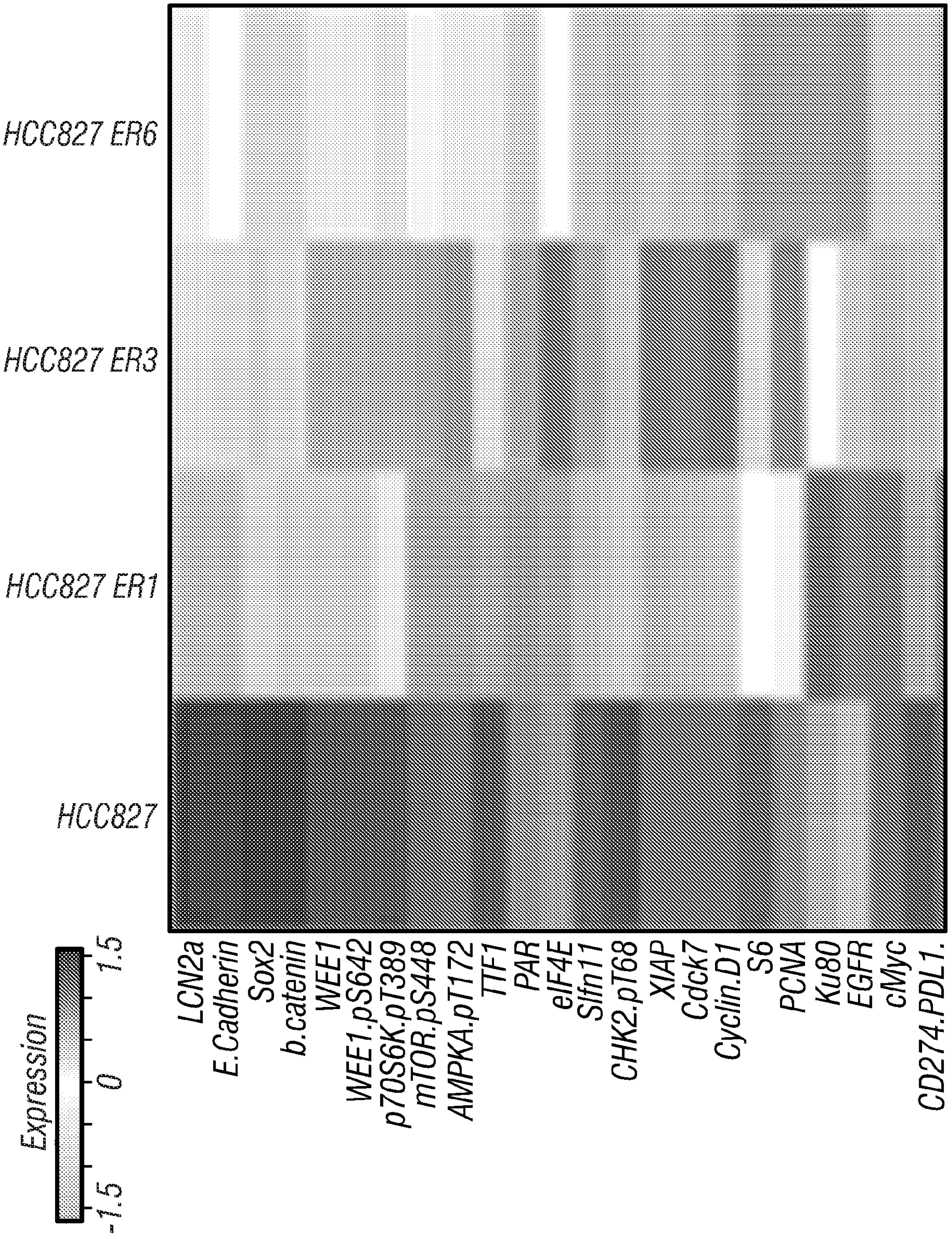
Figure 2D:
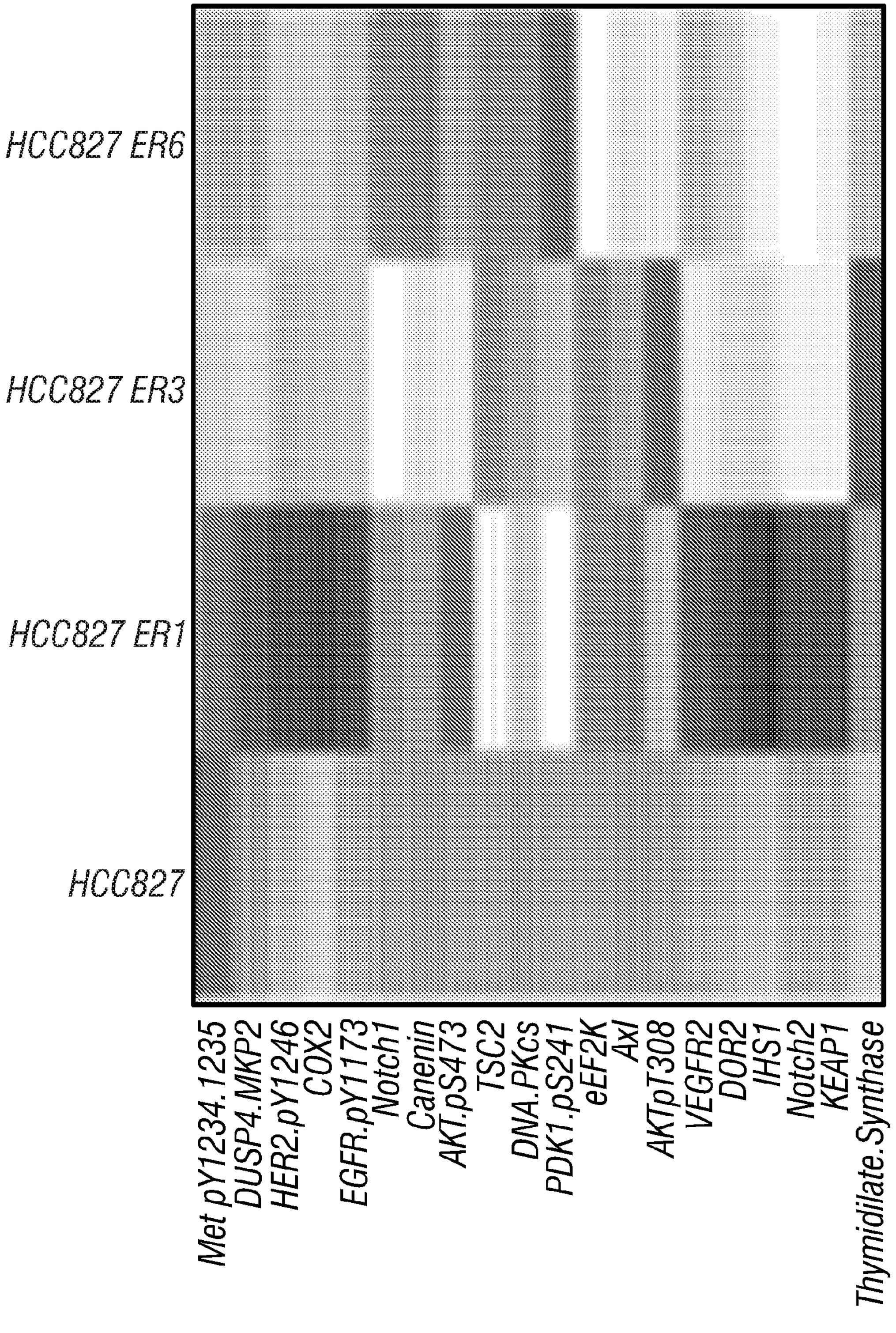
Figure 2D:
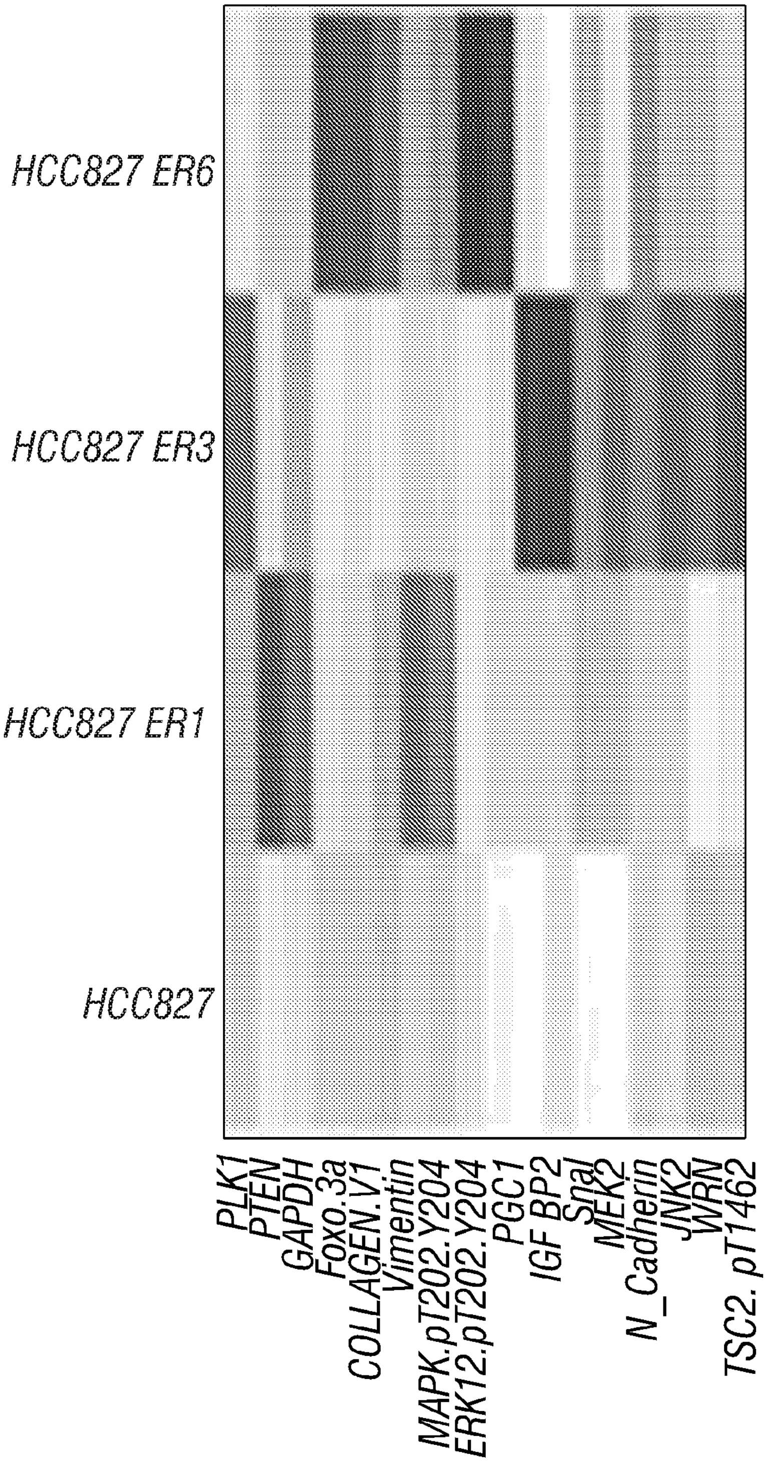
Figure 2D:
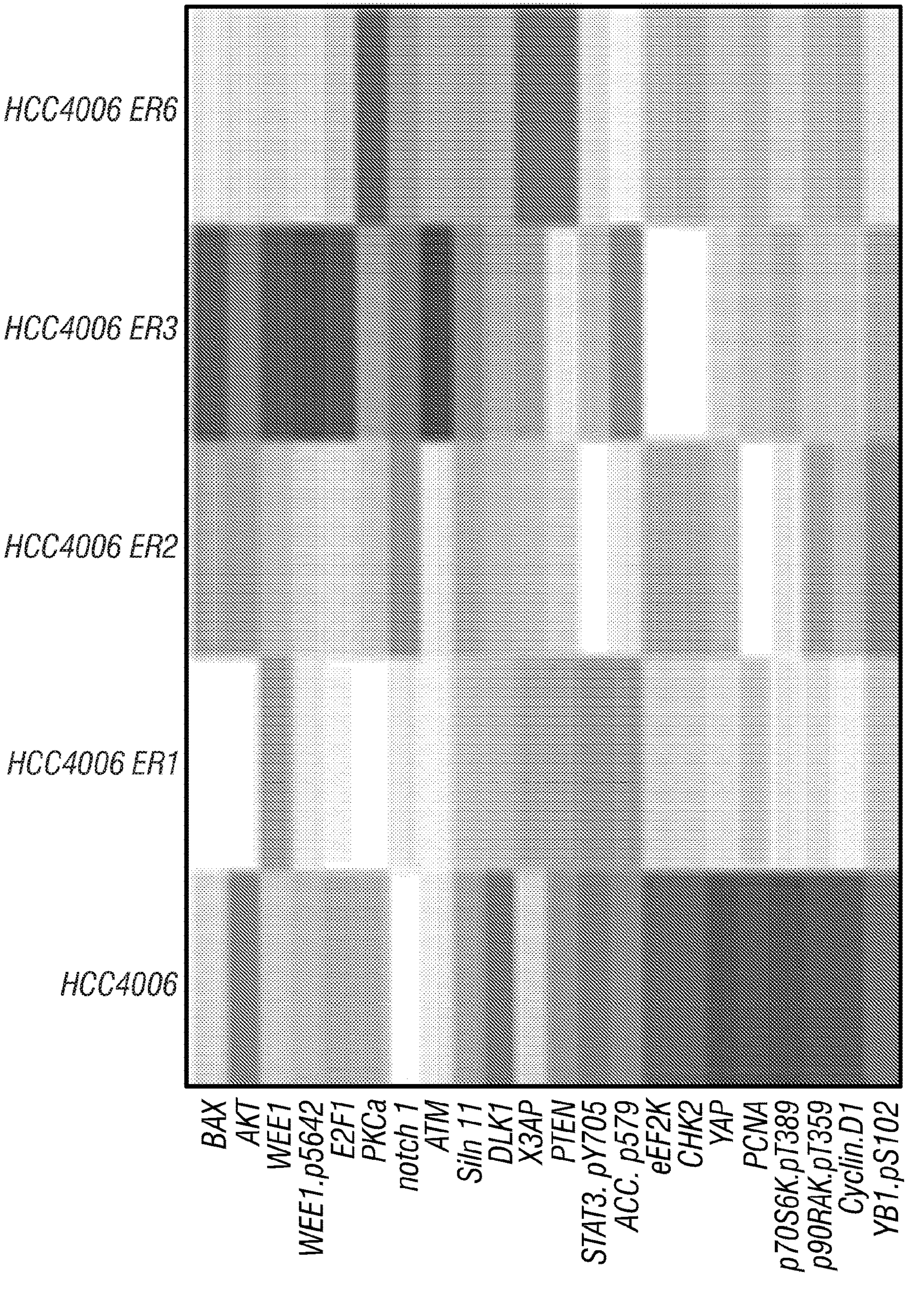
Figure 2D:
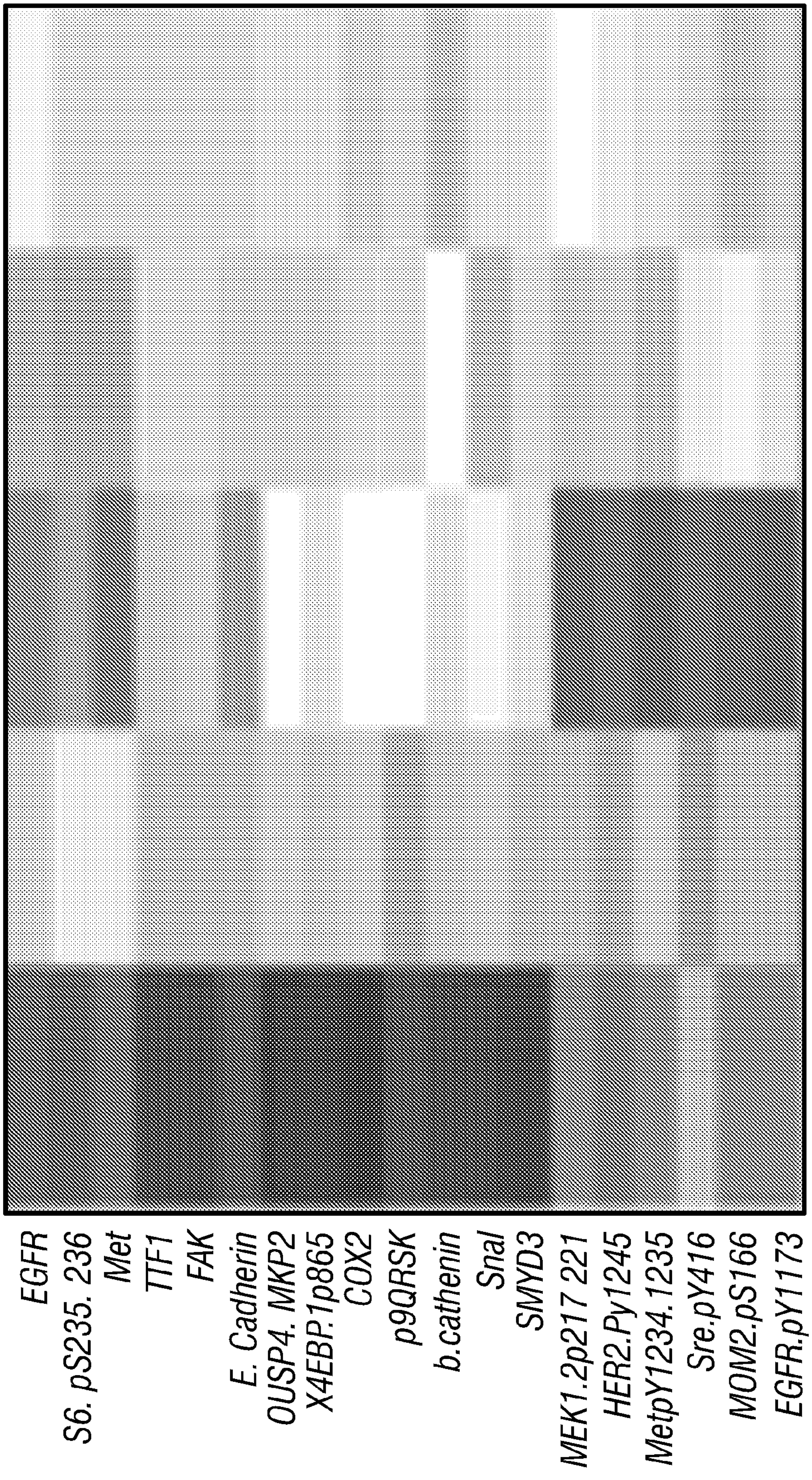
Figure 2D:
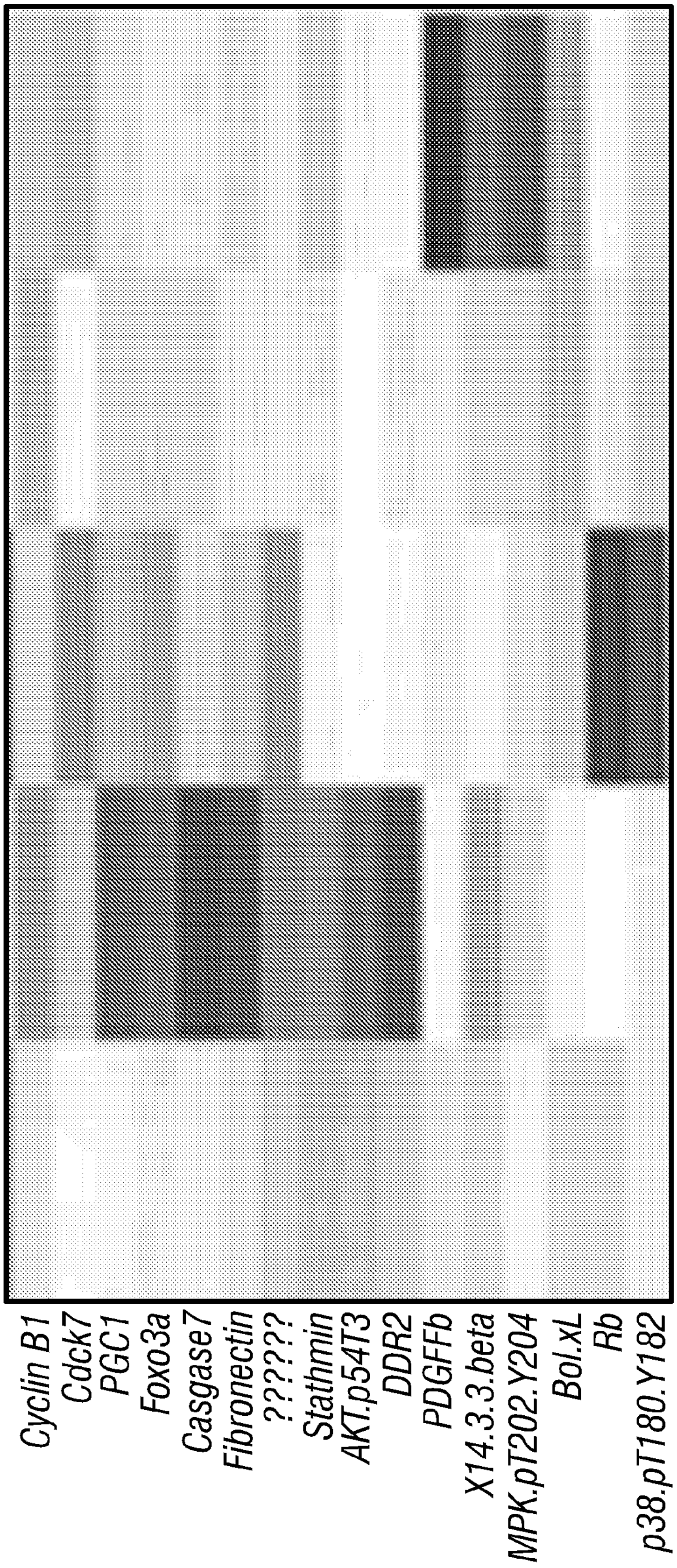
Figure 3A:
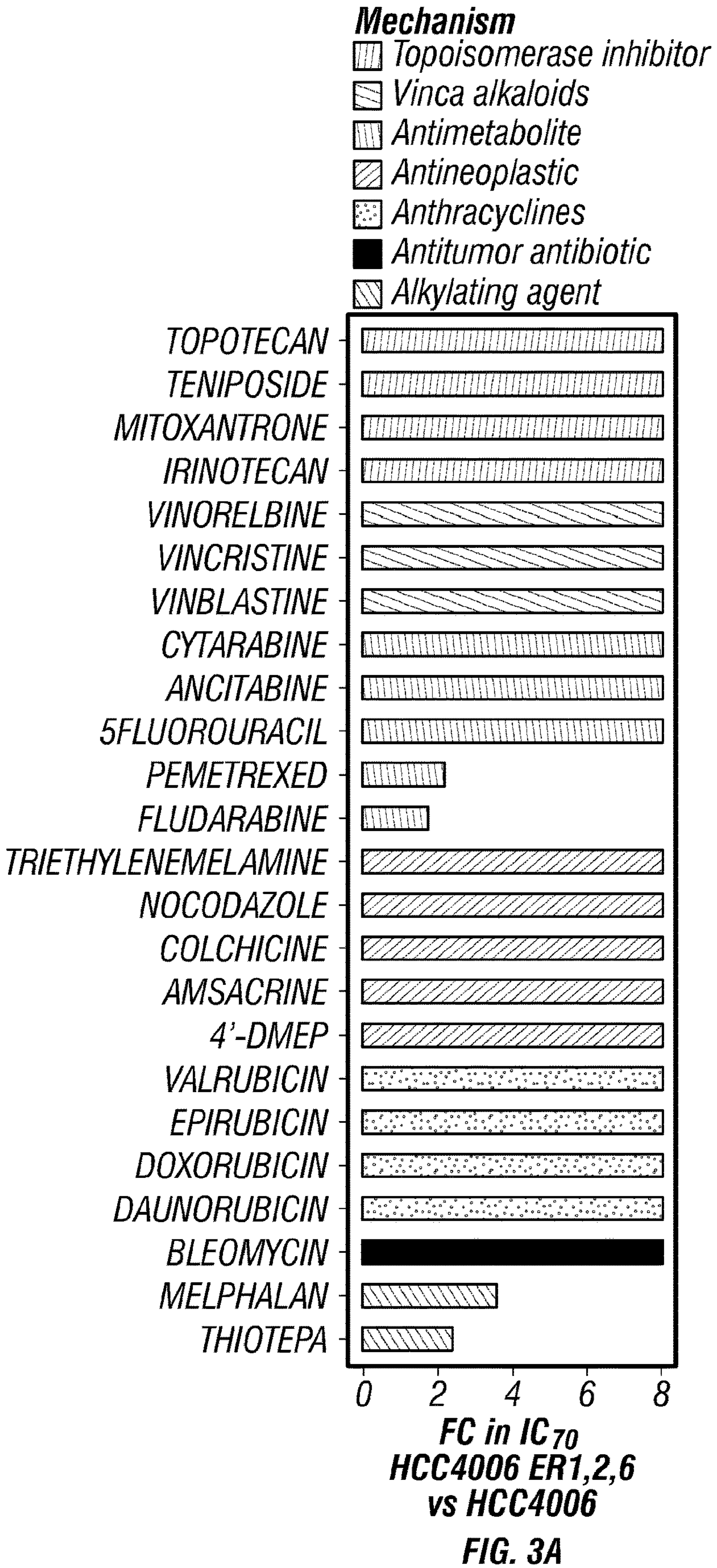
FIGS. 3A-3C: High throughput drug screening was performed to test the efficacy of 1,321 compounds. EGFR TKI resistant cells that have undergone EMT have acquired broad spectrum drug resistance to chemotherapeutic agents (A), serine/threonine kinase inhibitors (B) and tyrosine kinase inhibitors (C).
Figure 3A:
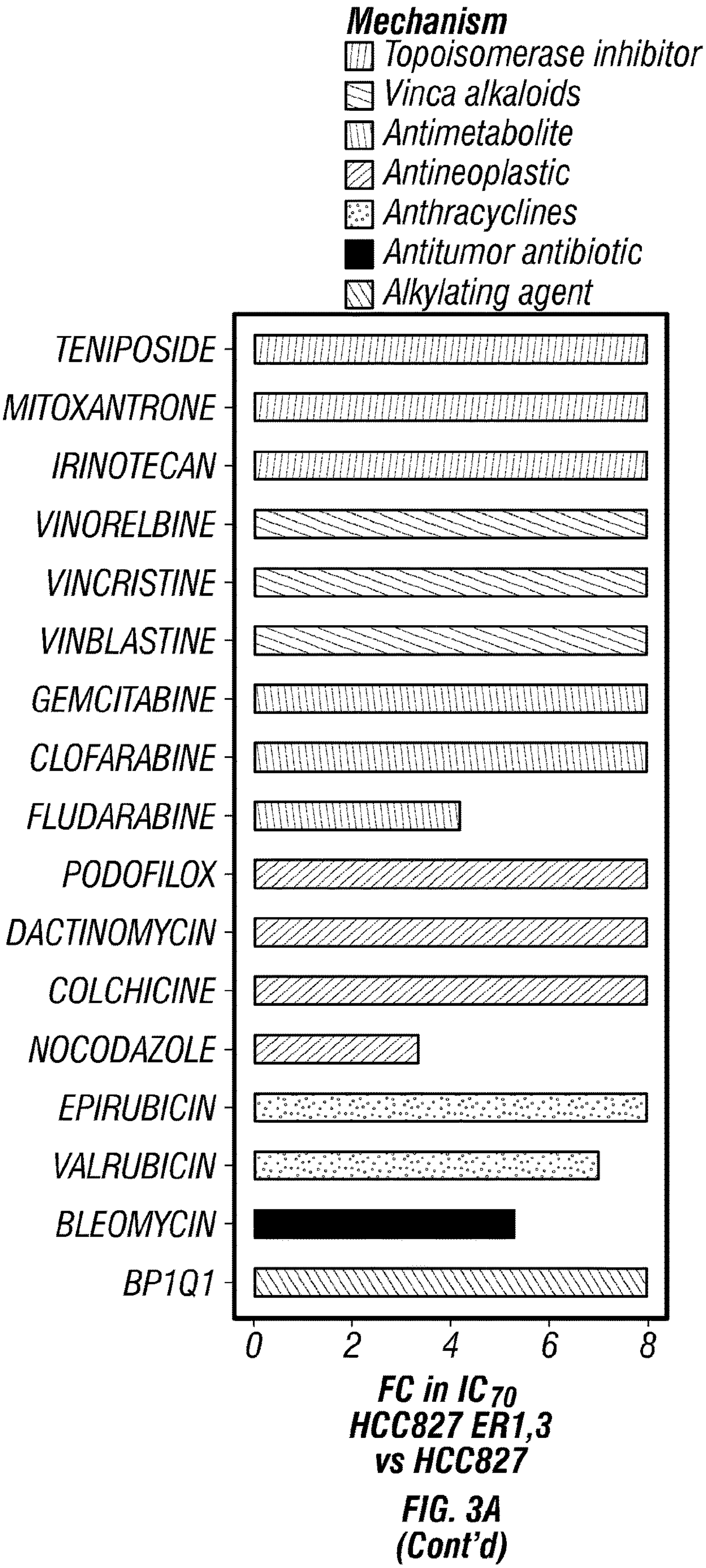
Figures 3B, 3C:
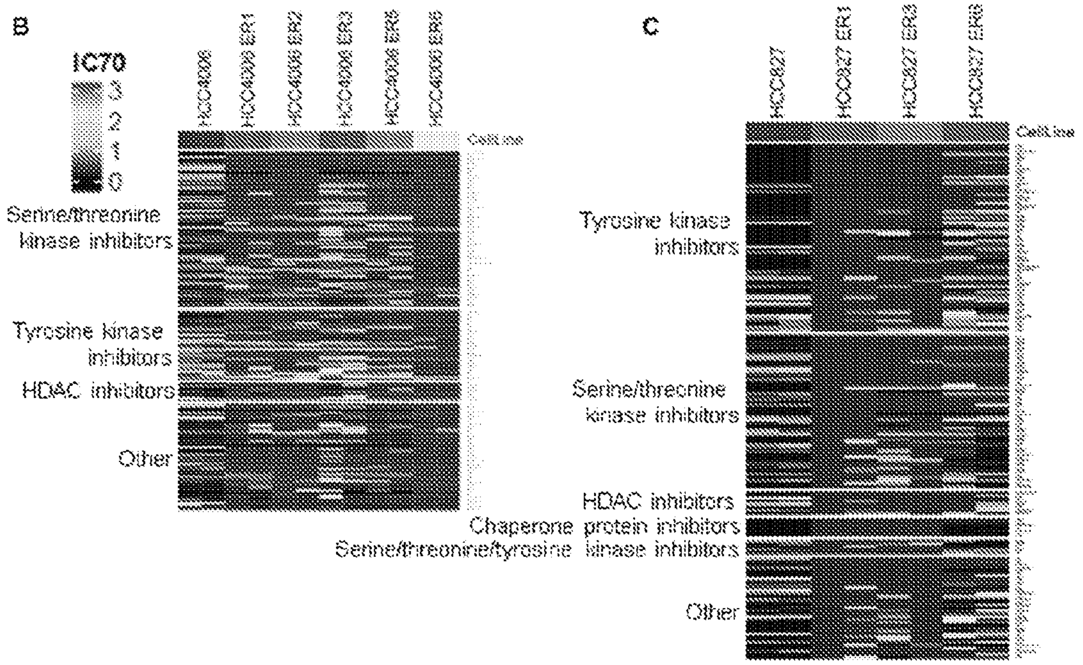
Figures 4A, 4B:
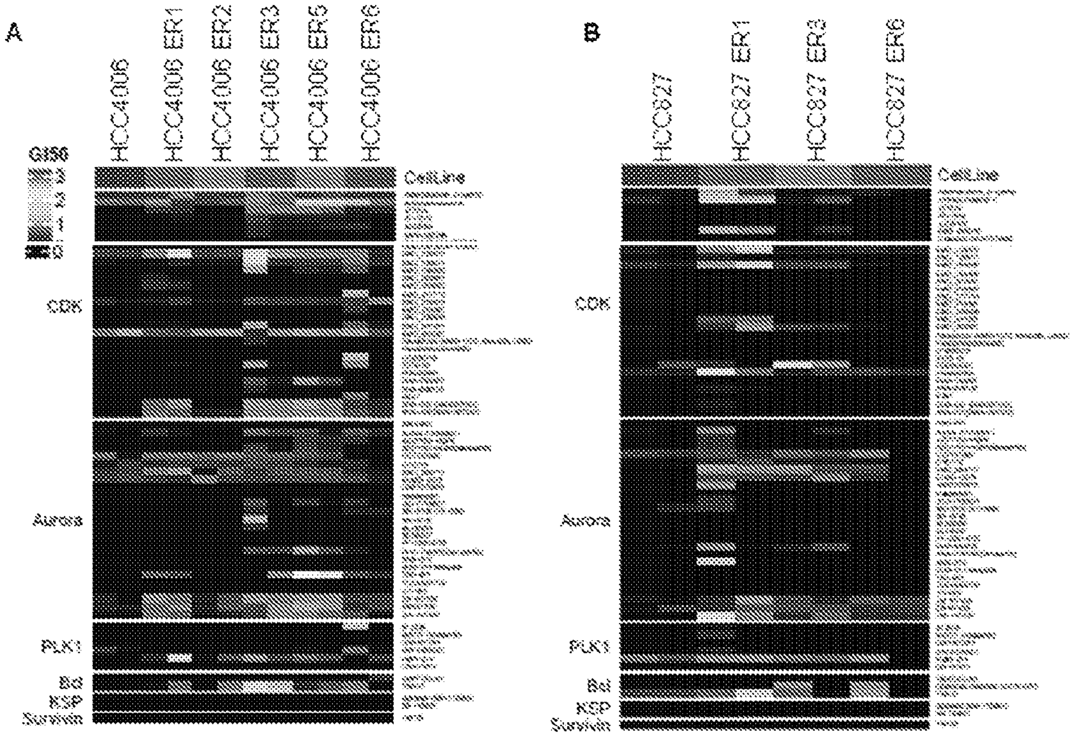
FIGS. 4A-4H: (A-B) High throughput drug screen analysis revealed that EGFR TKI resistant cells exhibit sustained sensitivity to agents targeting cyclin dependent kinases (CDK), Aurora kinase, polo-like kinase 1 (PLK1), Bcl, KSP and survivin. (C) Protein expression of PLK1, Aurora-A, Survivin and KSP in EGFR TKI resistant cells as determined by Western blotting. (D) EGFR TKI resistant cells were treated with increasing concentrations of inhibitors of Aurora kinase (alisertib, AMG900), PLK1 (volasertib), or KSP (ispinesib) for two weeks and viability was evaluated by clonogenic assay. (E-H) Quantification of clonogenic assays reveals that tumor cell viability is significantly inhibited following treatment with inhibitors targeting Aurora kinase, PLK1, and KSP.
Figure 4C:
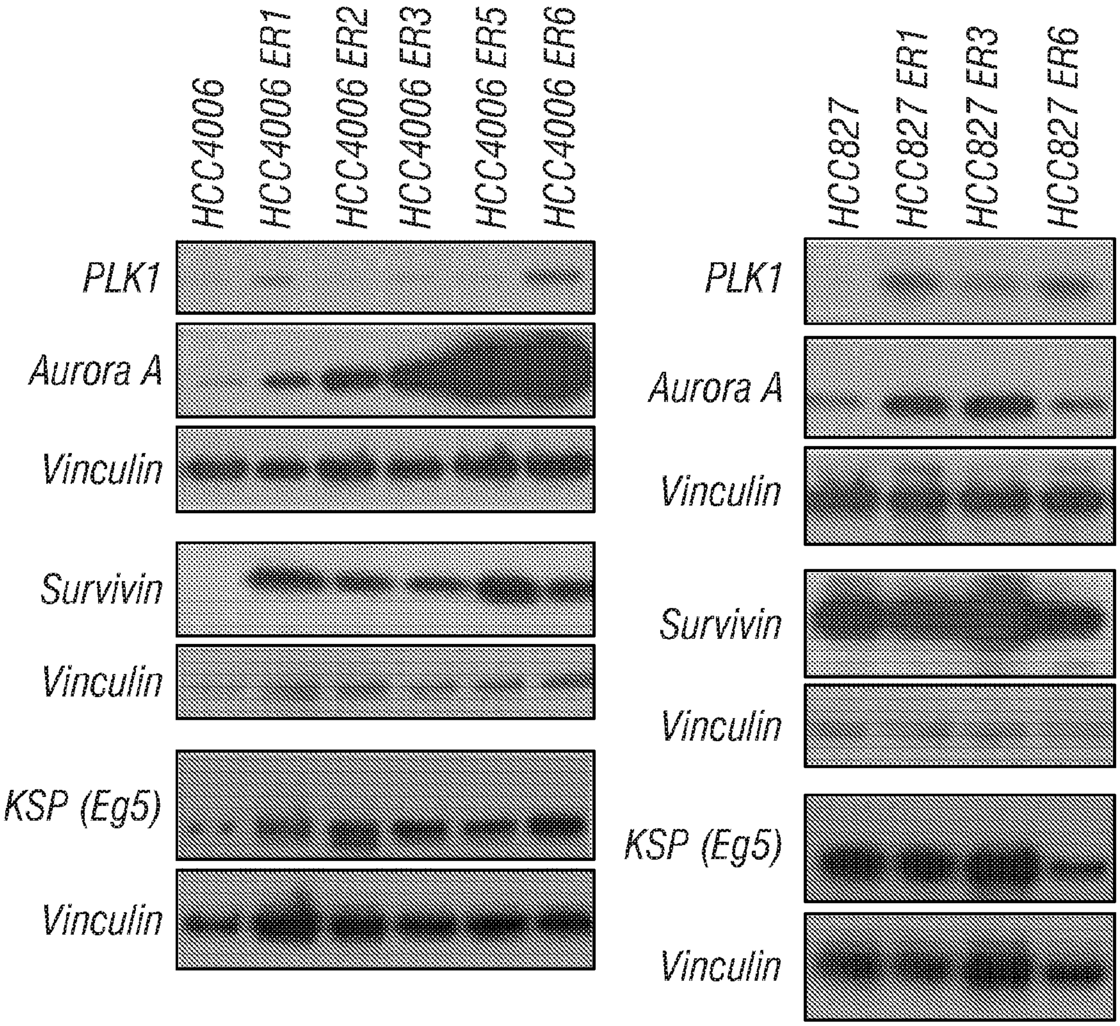
Figure 4D:
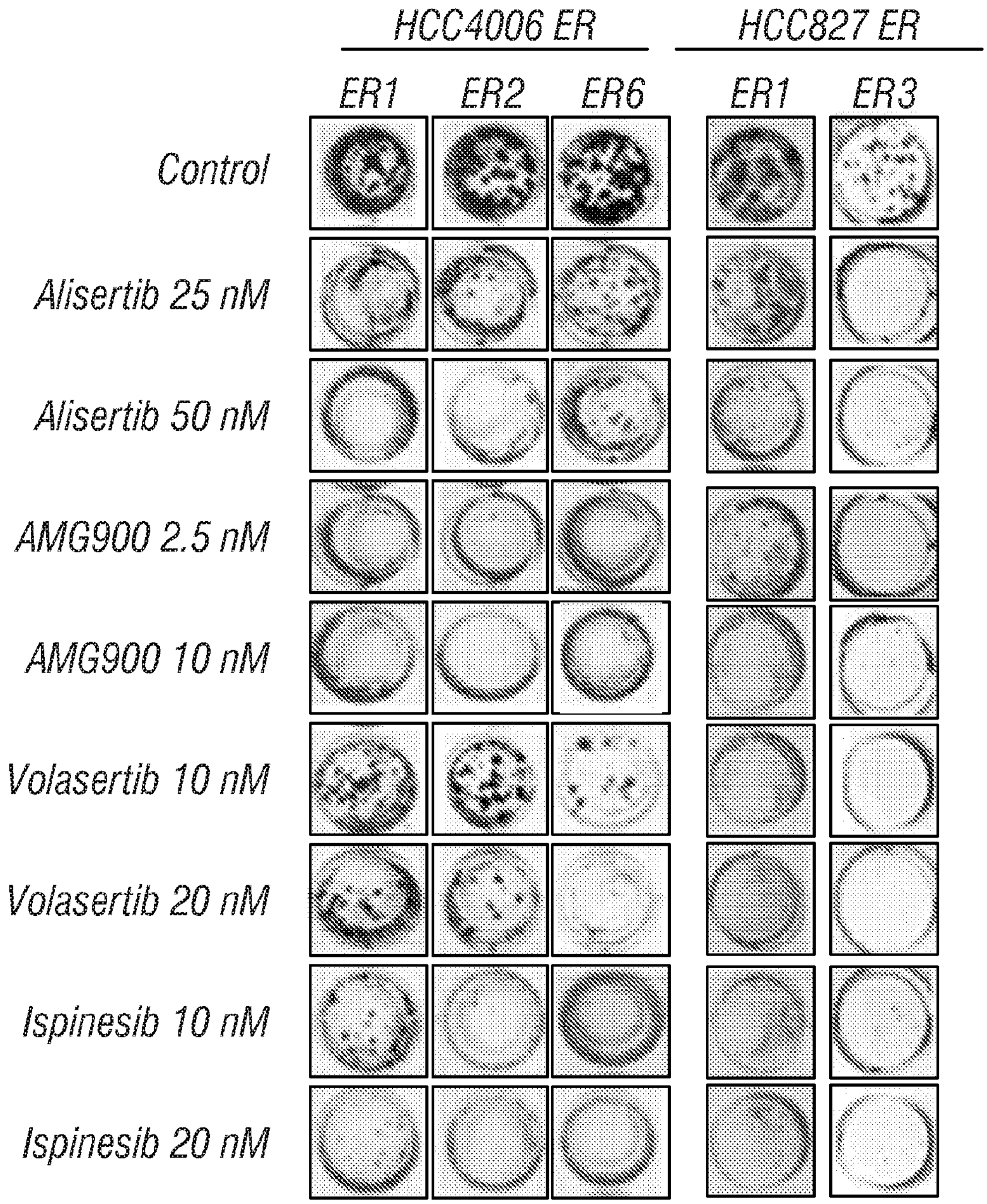
Figure 4E:
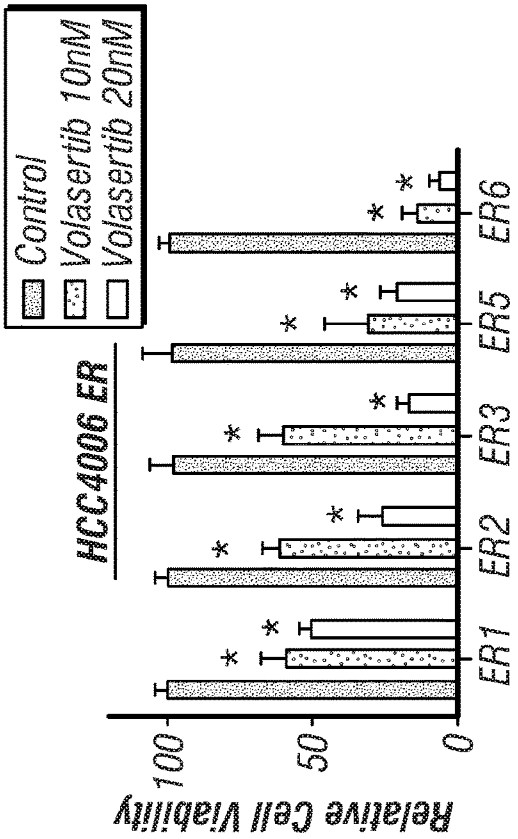
Figure 4F:
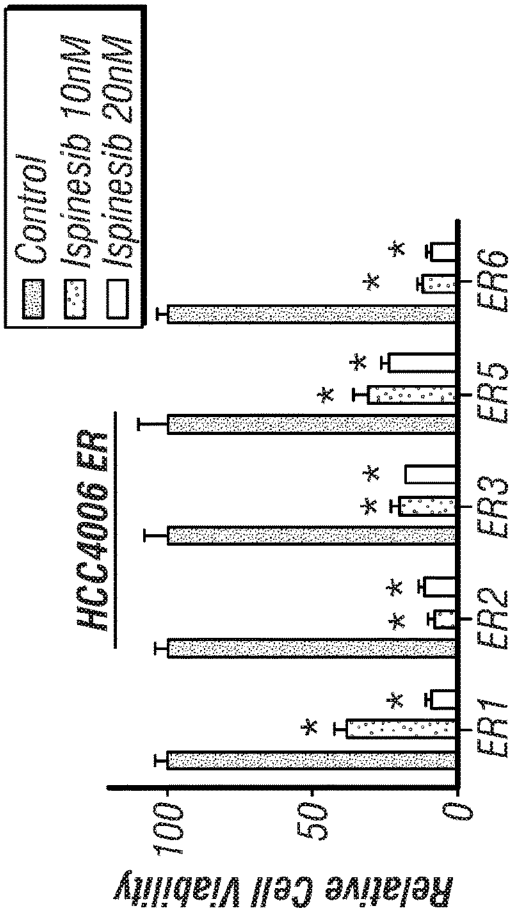
Figure 4G:
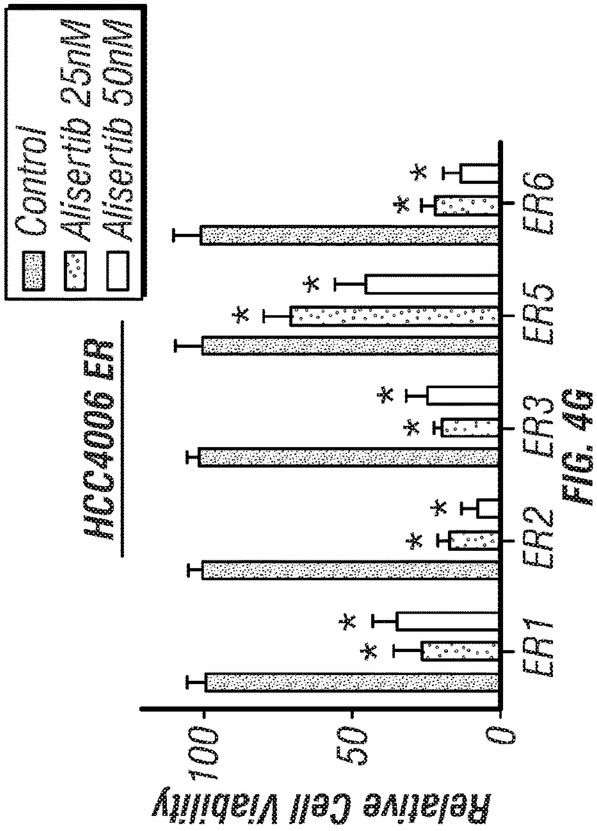
Figure 4H:
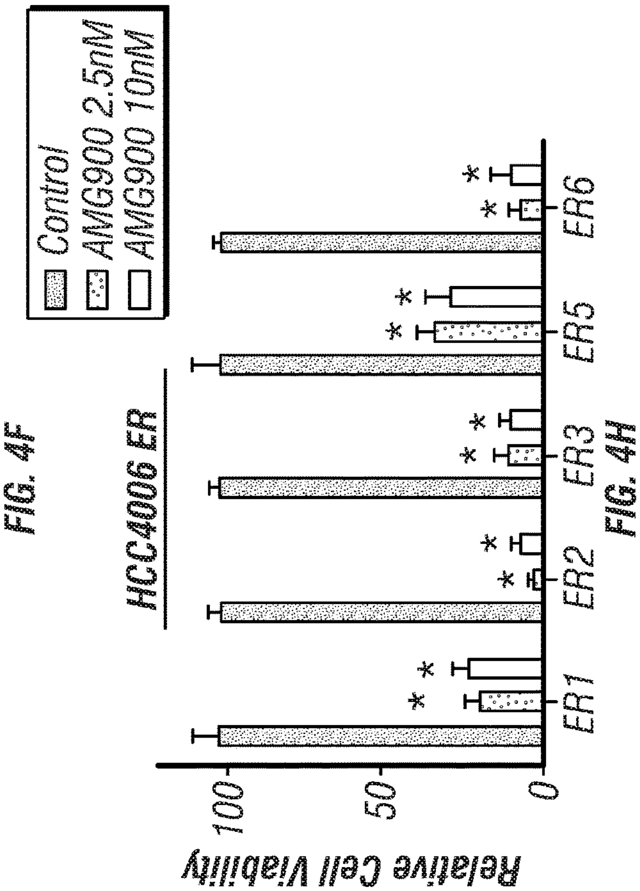
Figure 5A:
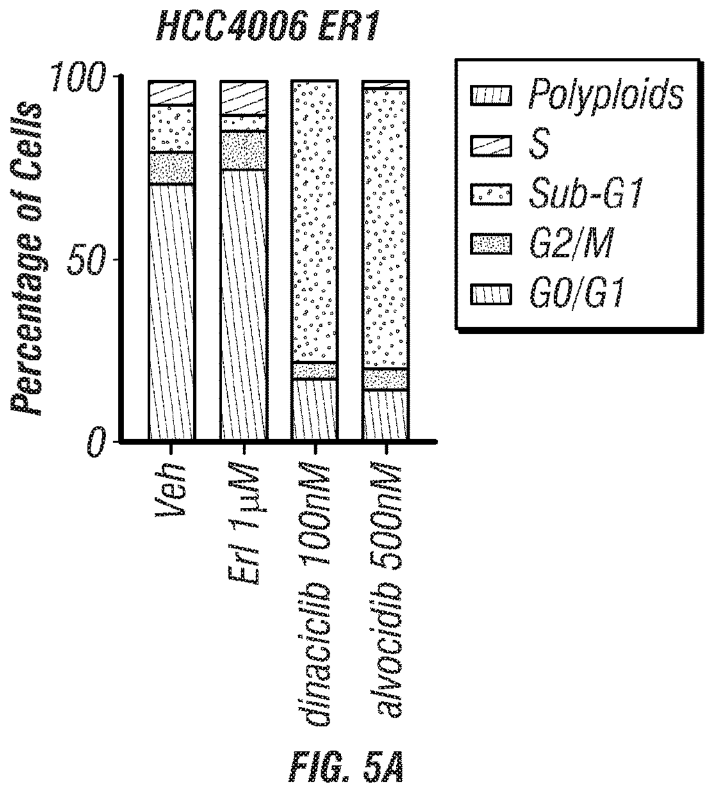
FIGS. 5A-5D: (A) Treatment of EGFR TKI resistant cells with CDK inhibitors dinaciclib or alvocidib significantly increases the percentage of sub-G1 cells as determined by PI staining and flow cytometry. (B) Inhibition of PLK1, KSP, or Aurora kinase results in G2/M arrest, increased sub-G1 populations, and increased percentage of polyploid cells. (C-D) Inhibition of CDK, PLK1, KSP, or Aurora kinase results in enhanced nuclear size.
Figure 5B:
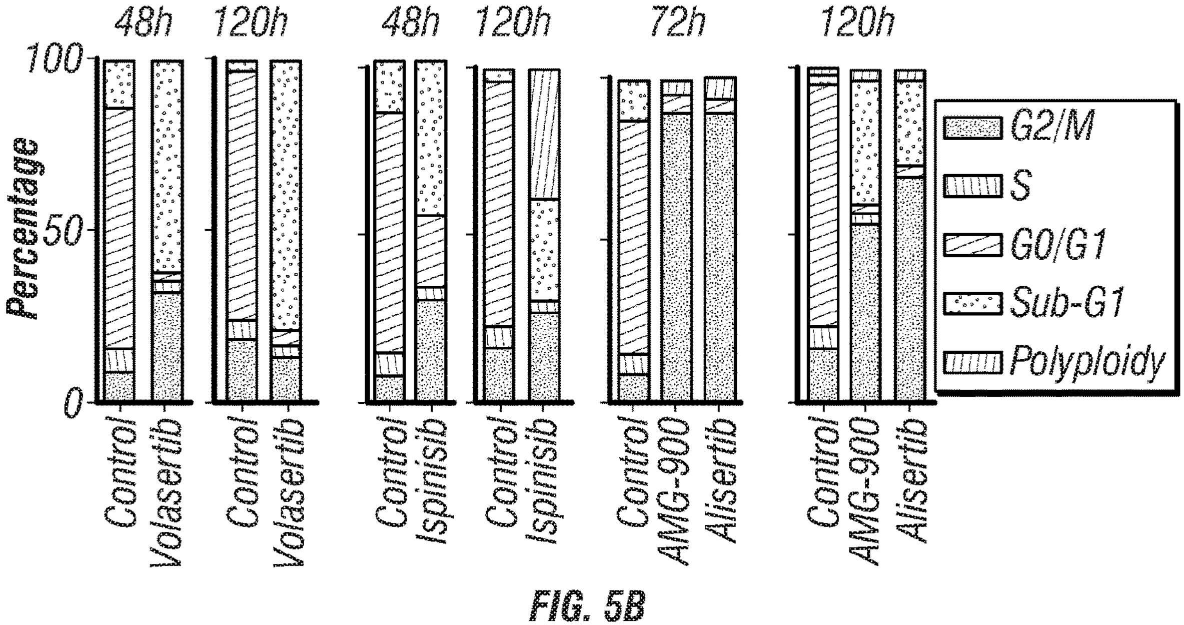
Figure 5C:
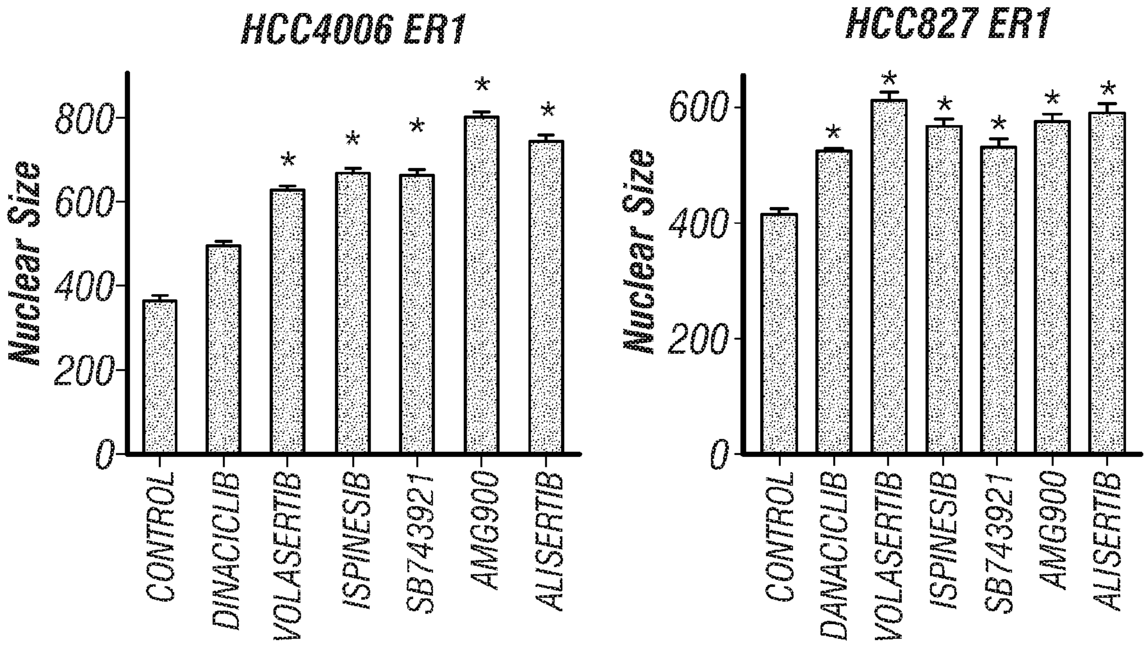
Figure 5D:
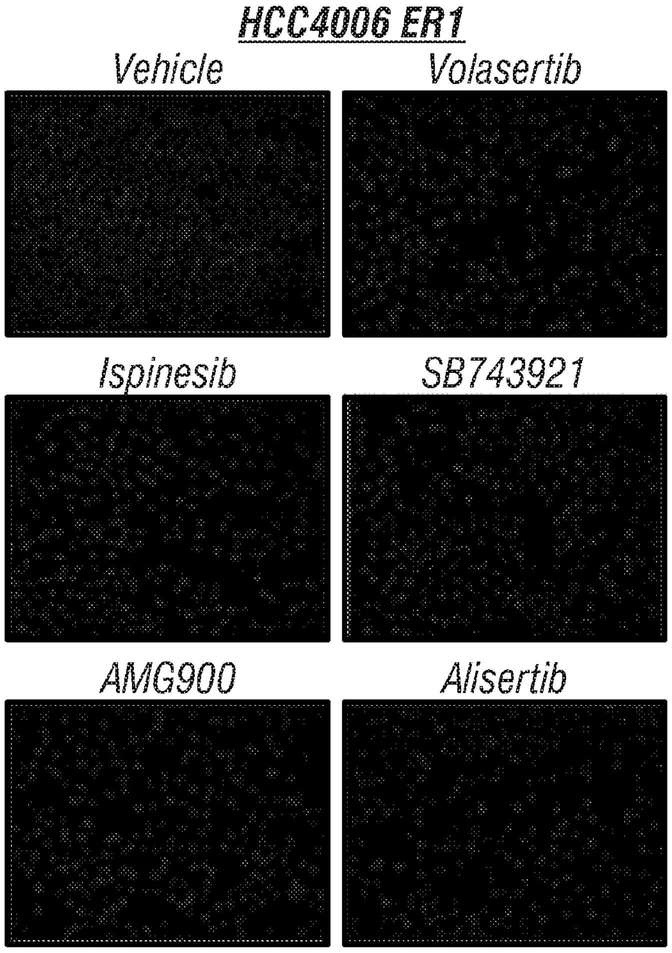
Figure 6A:
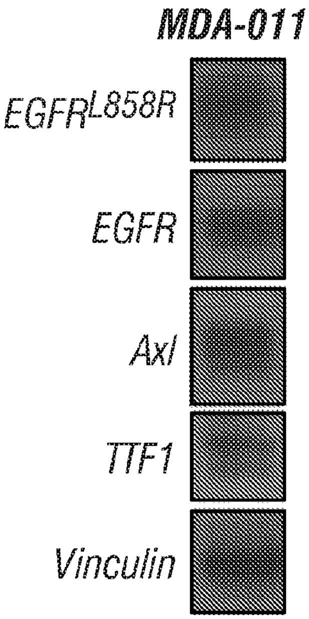
FIGS. 6A-6D: The patient-derived NSCLC cell line, MDA-011, expresses $EGFR^{L55SR}$ (A) and markers indicating a mesenchymal phenotype (B), and is resistant to erlotinib and osimertinib (C). (D) MDA-11 cells are sensitive to inhibitors of CDK (dinicacilib, alvocidib), PLK1 (volasertib, ON-01910), KSP (ispinesib, SB743921) and Aurora A (AMG900, Alisertib).
Figure 6B:
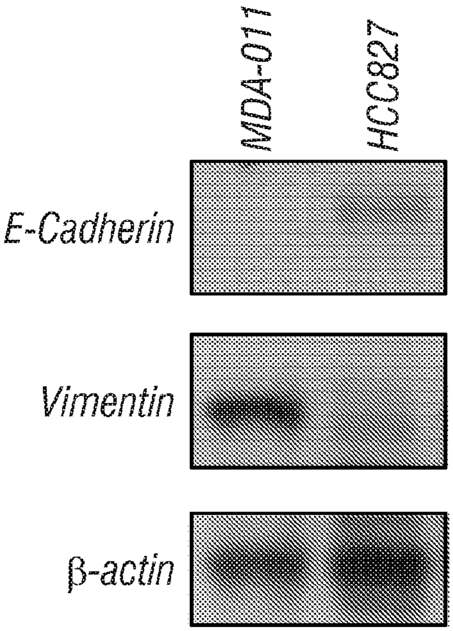
Figure 6C:
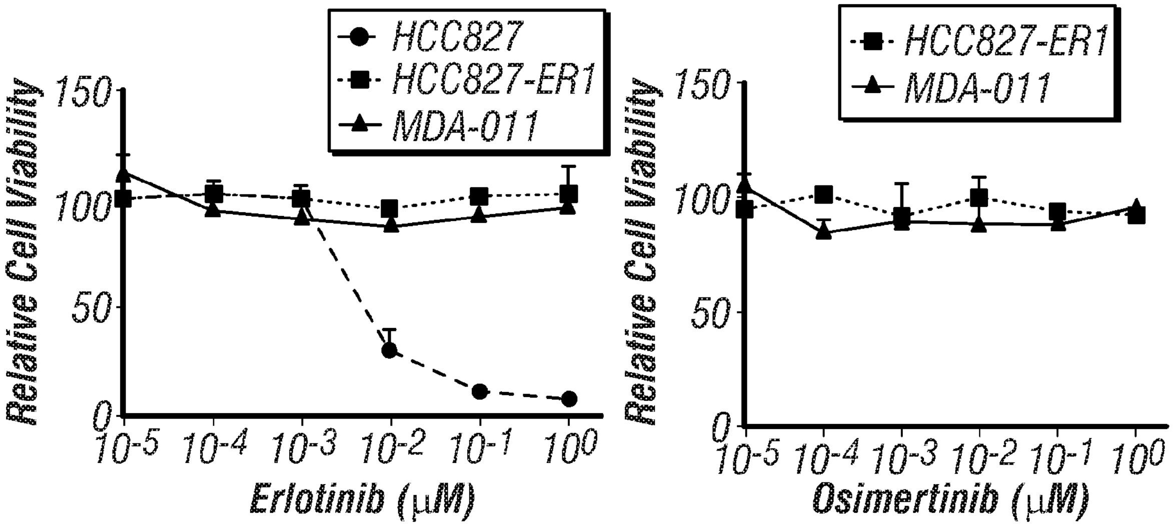
Figure 6D:
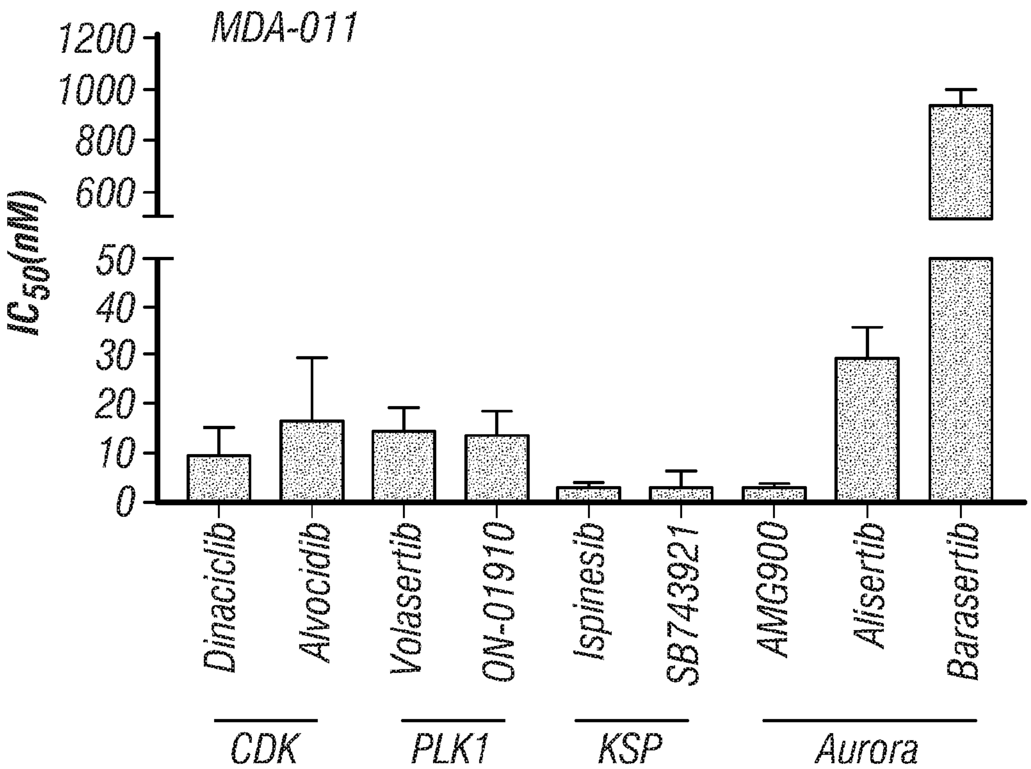

To address the unmet need for treatment regimens for TKI-resistant cancer, a panel of NSCLC cell lines with acquired resistance to the EGFR TKI, erlotinib, were derived in the present studies. A subset of EGFR TKI resistant variants was negative for secondary EGFR mutations, were resistant to 2nd and 3rd generation EGFR TKIs including osimertinb, afatinib, and dacomitinib, and had undergone epithelial to mesenchymal transition (EMT) as demonstrated by loss of E-cadherin, enhanced expression of N-cadherin and Axl and an increased invasive phenotype as determined by Boyden chamber assay. Proteomic profiling revealed that although EGFR TKI resistant cells displayed similar mesenchymal and invasive phenotypes, there was significant heterogeneity in protein expression and pathway activation among resistant variants derived from the same parental cell line.

To identify therapeutic agents with activity against EMT-associated EGFR TKI resistance, a high-throughput drug screening was performed to test the efficacy of 1,321 compounds. EMT-associated EGFR TKI resistance was accompanied by the acquisition of broad-spectrum drug resistance. Compared to parental cells, mesenchymal EGFR TKI resistant cells were significantly more resistant to chemotherapeutic agents used to treat NSCLC including pemetrexed, irinotecan, vinblastine, and gemcitabine. EGFR TKI resistant cells displayed acquired resistance to 147 other tyrosine kinase and serine/threonine kinase inhibitors. In contrast, both parental cells and mesenchymal EGFR TKI resistant variants were highly sensitive to CDK inhibitors and agents targeting spindle assembly checkpoint (SAC) components including PLK1, Aurora, KSP, and survivin. These finding were validated by MTS and clonogenic assays. Treatment with SAC inhibitors induced the accumulation of cells in G2/M phase, enlarged nuclear size, and polyploidy.

To clinically validate these findings, a cell line (MDA-011) was established from the pleural effusion of an EGFR mutant NSCLC patient with T790M-negative resistance to erlotinib. In vitro, MDA-011 cells were resistant to erlotinib and osimertinib. MDA-011 cells were highly sensitive to CDK inhibitors and SAC inhibitors as determined by MTS and clonogenic assays. These data indicated that EMT-associated resistance to EGFR TKIs is associated with broad spectrum drug resistance but vulnerabilities to CDK and SAC inhibition can potentially be exploited to overcome resistant disease in NSCLC patients.

Accordingly, in certain embodiments, the present disclosure provides methods for treating cancers with activating EGFR mutations, such as NSCLC, with inhibitor of CDK and/or inhibitor of SAC components. The EGFR mutant NSCLC cells may or may not have acquired resistance to EGFR TKIs. Exemplary CDK inhibitors include diniciclib and alvocidib, and exemplary agents targeting spindle assembly checkpoint (SAC) components include PLK1 (volasertib), Aurora A (AMG-900 and alisertib), and KSP (ispinesib). In some aspects, the cancer, such as NSCLC, cells express EGFR activating mutations such as L858R, exon 19 deletions, and exon 20 insertions. The cancer cells may have acquired resistance to EGFR TKIs and/or broad-spectrum drug resistance, such as due to T790M mutation and/or epithelial to mesenchymal transition.

I. DEFINITIONS

An "EGFR activating mutation" is referred to herein as somatic mutation(s) that can lead to the development of cancer, such as lung cancer, and are found in exons 18-21 of EGFR. Exemplary EGFR activating mutations include single-nucleotide substitutions, such as L858R, V765A, T783, or G719 change to serine, alanine, or cysteine, exon 19 deletion(s) (e.g., in-frame deletions of exon 19 between L747 to L749), and exon 20 insertion(s) and/or duplication(s) (e.g., D770_N771 (ins NPG), D770_(ins SVQ) and D770_(ins G) N771T). Other "resistance mutations" may be acquired, such as T790M.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more. The terms "about", "substantially" and "approximately" mean, in general, the stated value plus or minus 5%.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human patients are adults, juveniles, infants and fetuses.

The term "effective," as that term is used in the specification and/or claims, means adequate to accomplish a desired, expected, or intended result. "Effective amount," "therapeutically effective amount" or "pharmaceutically effective amount" when used in the context of treating a patient or subject with a compound means that amount of the compound which, when administered to a subject or patient for treating or preventing a disease, is an amount sufficient to affect such treatment or prevention of the disease.

As used herein, the term "$IC_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "anti-cancer" agent is capable of negatively affecting a cancer cell/tumor in a subject, for example, by promoting killing of cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer.

The term "insertion(s)" or "insertion mutation(s)" refers to the addition of one or more nucleotide base pairs into a DNA sequence. For example, an insertion mutation of exon 20 of EGFR can occur between amino acids 767 to 774, of about 2-21 base pairs.

"Detection," "detectable" and grammatical equivalents thereof refer to ways of determining the presence and/or quantity and/or identity of a target nucleic acid sequence. In some embodiments, detection occurs amplifying the target nucleic acid sequence. In other embodiments, sequencing of the target nucleic acid can be characterized as "detecting" the target nucleic acid. A label attached to the probe can include any of a variety of different labels known in the art that can be detected by, for example, chemical or physical means. Labels that can be attached to probes may include, for example, fluorescent and luminescence materials.

"Amplifying," "amplification," and grammatical equivalents thereof refers to any method by which at least a part of a target nucleic acid sequence is reproduced in a template-dependent manner, including without limitation, a broad range of techniques for amplifying nucleic acid sequences, either linearly or exponentially. Exemplary means for performing an amplifying step include ligase chain reaction (LCR), ligase detection reaction (LDR), ligation followed by Q-replicase amplification, PCR, primer extension, strand displacement amplification (SDA), hyperbranched strand displacement amplification, multiple displacement amplification (MDA), nucleic acid strand-based amplification (NASBA), two-step multiplexed amplifications, rolling circle amplification (RCA), recombinase-polymerase amplification (RPA) (TwistDx, Cambridg, UK), and self-sustained sequence replication (3SR), including multiplex versions or combinations thereof, for example but not limited to, OLA/PCR, PCR/OLA, LDR/PCR, PCR/PCR/LDR, PCR/LDR, LCR/PCR, PCR/LCR (also known as combined chain reaction-CCR), and the like. Descriptions of such techniques can be found in, among other places, Sambrook et al. Molecular Cloning, $3^{rd}$ Edition).

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Non-limiting examples of such salts include acid addition salts formed with inorganic acids such as hydrochloric acid, hydrobromic acid, sulfuric acid, nitric acid, and phosphoric acid; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, and trimethylacetic acid. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Non-limiting examples of acceptable organic bases include ethanolamine, diethanolamine, triethanolamine, tromethamine, and N-methylglucamine It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

II. EGFR ACTIVATING MUTATIONS

Certain embodiments of the present disclosure concern determining if a subject has one or more EGFR activating mutations, such as L858R, exon 19 deletion(s), or exon 20 mutation(s), such as an insertion mutation, particularly one or more insertion mutations. The subject may have 2, 3, 4, or more activating EGFR mutations. Mutation detection methods are known the art including PCR analyses and nucleic acid sequencing as well as FISH and CGH. In particular aspects, the exon 20 mutations are detected by DNA sequencing, such as from a tumor or circulating free DNA from plasma.

The EGFR exon 19 mutation(s) may comprise one or more point mutations, insertions, and/or deletions of 3-18 nucleotides between amino acids in-frame deletions of exon 19 between 747-749.

The EGFR exon 20 mutation(s) may comprise one or more point mutations, insertions, and/or deletions of 3-18 nucleotides between amino acids 763-778. The one or more EGFR exon 20 mutations may be located at one or more residues selected from the group consisting of A763, A767, 5768, V769, D770, N771, P772, and H773.

EGFR exon 20 insertions may include H773_V774insH, A767_v769ASV, N771_P772insH, D770_N771insG, H779_V774insH, N771delinsHH, S768_D770dupDVD, A767_V769dupASV, A767_V769dupASV, P772_H773dup, N771_H773dupNPH, S768_D770dupSVD, N771delinsGY, S768_D770delinsSVD, D770_D770delinsGY, A767_V769dupASV, and/or H773dup. In particular aspects, the exon 20 mutations are A763insFQEA, A767insASV, S768dupSVD, V769insASV, D770insSVD, D770insNPG, H773insNPH, N771del insGY, N771del insFH and/or N771dupNPH.

The patient sample can be any bodily tissue or fluid that includes nucleic acids from the lung cancer in the subject. In certain embodiments, the sample will be a blood sample comprising circulating tumor cells or cell free DNA. In other embodiments, the sample can be a tissue, such as a lung tissue. The lung tissue can be from a tumor tissue and may be fresh frozen or formalin-fixed, paraffin-embedded (FFPE). In certain embodiments, a lung tumor FFPE sample is obtained.

Samples that are suitable for use in the methods described herein contain genetic material, e.g., genomic DNA (gDNA). Genomic DNA is typically extracted from biological samples such as blood or mucosal scrapings of the lining of the mouth, but can be extracted from other biological samples including urine, tumor, or expectorant. The sample itself will typically include nucleated cells (e.g., blood or buccal cells) or tissue removed from the subject including normal or tumor tissue. Methods and reagents are known in the art for obtaining, processing, and analyzing samples. In some embodiments, the sample is obtained with the assistance of a health care provider, e.g., to draw blood. In some embodiments, the sample is obtained without the assistance of a health care provider, e.g., where the sample is obtained non-invasively, such as a sample comprising buccal cells that is obtained using a buccal swab or brush, or a mouthwash sample.

In some cases, a biological sample may be processed for DNA isolation. For example, DNA in a cell or tissue sample can be separated from other components of the sample. Cells can be harvested from a biological sample using standard techniques known in the art. For example, cells can be harvested by centrifuging a cell sample and resuspending the pelleted cells. The cells can be resuspended in a buffered solution such as phosphate-buffered saline (PBS). After centrifuging the cell suspension to obtain a cell pellet, the cells can be lysed to extract DNA, e.g., gDNA. See, e.g., Ausubel et al. (2003). The sample can be concentrated and/or purified to isolate DNA. All samples obtained from a subject, including those subjected to any sort of further processing, are considered to be obtained from the subject. Routine methods can be used to extract genomic DNA from a biological sample, including, for example, phenol extraction. Alternatively, genomic DNA can be extracted with kits such as the QIAamp® Tissue Kit (Qiagen, Chatsworth, Calif.) and the Wizard® Genomic DNA purification kit (Promega). Non-limiting examples of sources of samples include urine, blood, and tissue.

The presence or absence of EGFR activating mutations as described herein can be determined using methods known in the art. For example, gel electrophoresis, capillary electrophoresis, size exclusion chromatography, sequencing, and/or arrays can be used to detect the presence or absence of insertion mutations. Amplification of nucleic acids, where desirable, can be accomplished using methods known in the art, e.g., PCR. In one example, a sample (e.g., a sample comprising genomic DNA), is obtained from a subject. The DNA in the sample is then examined to determine the identity of an insertion mutation as described herein. An insertion mutation can be detected by any method described herein, e.g., by sequencing or by hybridization of the gene in the genomic DNA, RNA, or cDNA to a nucleic acid probe, e.g., a DNA probe (which includes cDNA and oligonucleotide probes) or an RNA probe. The nucleic acid probe can be designed to specifically or preferentially hybridize with a particular variant.

A set of probes typically refers to a set of primers, usually primer pairs, and/or detectably-labeled probes that are used to detect the target genetic variations (e.g., EGFR activating mutations) used in the actionable treatment recommendations of the present disclosure. The primer pairs are used in an amplification reaction to define an amplicon that spans a region for a target genetic variation for each of the aforementioned genes. The set of amplicons are detected by a set of matched probes. In an exemplary embodiment, the present methods may use TaqMan™ (Roche Molecular Systems, Pleasanton, Calif.) assays that are used to detect a set of target genetic variations, such as EGFR activating mutations. In one embodiment, the set of probes are a set of primers used to generate amplicons that are detected by a nucleic acid sequencing reaction, such as a next generation sequencing reaction. In these embodiments, for example, AmpliSEQ™ (Life Technologies/Ion Torrent, Carlsbad, Calif.) or TruSEQ™ (Illumina, San Diego, Calif.) technology can be employed.

Analysis of nucleic acid markers can be performed using techniques known in the art including, without limitation, sequence analysis, and electrophoretic analysis. Non-limiting examples of sequence analysis include Maxam-Gilbert sequencing, Sanger sequencing, capillary array DNA sequencing, thermal cycle sequencing (Sears et al., 1992), solid-phase sequencing (Zimmerman et al., 1992), sequencing with mass spectrometry such as matrix-assisted laser desorption/ionization time-of-flight mass spectrometry (MALDI-TOF/MS; Fu et al., 1998), and sequencing by hybridization (Chee et al., 1996; Drmanac et al., 1993; Drmanac et al., 1998). Non-limiting examples of electrophoretic analysis include slab gel electrophoresis such as agarose or polyacrylamide gel electrophoresis, capillary electrophoresis, and denaturing gradient gel electrophoresis. Additionally, next generation sequencing methods can be performed using commercially available kits and instruments from companies such as the Life Technologies/Ion Torrent PGM or Proton, the Illumina HiSEQ or MiSEQ, and the Roche/454 next generation sequencing system.

Other methods of nucleic acid analysis can include direct manual sequencing (Church and Gilbert, 1988; Sanger et al., 1977; U.S. Pat. No. 5,288,644); automated fluorescent sequencing; single-stranded conformation polymorphism assays (SSCP) (Schafer et al., 1995); clamped denaturing gel electrophoresis (CDGE); two-dimensional gel electrophoresis (2DGE or TDGE); conformational sensitive gel electrophoresis (CSGE); denaturing gradient gel electrophoresis (DGGE) (Sheffield et al., 1989); denaturing high performance liquid chromatography (DHPLC, Underhill et al., 1997); infrared matrix-assisted laser desorption/ionization (IR-MALDI) mass spectrometry (WO 99/57318); mobility shift analysis (Orita et al., 1989); restriction enzyme analysis (Flavell et al., 1978; Geever et al., 1981); quantitative real-time PCR (Raca et al., 2004); heteroduplex analysis; chemical mismatch cleavage (CMC) (Cotton et al., 1985); RNase protection assays (Myers et al., 1985); use of polypeptides that recognize nucleotide mismatches, e.g., *E. coli* mutS protein; allele-specific PCR, and combinations of such methods. See, e.g., U.S. Patent Publication No. 2004/0014095, which is incorporated herein by reference in its entirety.

In one example, a method of identifying an EGFR activating mutation in a sample comprises contacting a nucleic acid from said sample with a nucleic acid probe that is capable of specifically hybridizing to nucleic acid encoding a mutated EGFR protein, or fragment thereof incorporating a mutation, and detecting said hybridization. In a particular embodiment, said probe is detectably labeled such as with a radioisotope ($^3$H, $^{32}$P, or $^{33}$P), a fluorescent agent (rhodamine, or fluorescein) or a chromogenic agent. In a particular embodiment, the probe is an antisense oligomer, for example PNA, morpholino-phosphoramidates, LNA or 2'-alkoxyalkoxy. The probe may be from about 8 nucleotides to about 100 nucleotides, or about 10 to about 75, or about 15 to about 50, or about 20 to about 30. In another aspect, said probes of the present disclosure are provided in a kit for identifying EGFR activating mutations in a sample, said kit comprising an oligonucleotide that specifically hybridizes to or adjacent to a site of mutation in the EGFR gene. The kit may further comprise instructions for treating patients having tumors that contain EGFR activating mutations with a CDK inhibitor and/or SAC inhibitor based on the result of a hybridization test using the kit.

In another aspect, a method for detecting an exon 20 mutation in a sample comprises amplifying from said sample nucleic acids corresponding to exon 20 of said EGFR gene, or a fragment thereof suspected of containing a mutation, and comparing the electrophoretic mobility of the amplified nucleic acid to the electrophoretic mobility of corresponding wild-type EGFR or fragment thereof. A difference in the mobility indicates the presence of a mutation in the amplified nucleic acid sequence. Electrophoretic mobility may be determined on polyacrylamide gel.

Alternatively, nucleic acids may be analyzed for detection of mutations using Enzymatic Mutation Detection (EMD) (Del Tito et al., 1998). EMD uses the bacteriophage resolvase $T_4$ endonuclease VII, which scans along double-stranded DNA until it detects and cleaves structural distortions caused by base pair mismatches resulting from point mutations, insertions and deletions. Detection of two short fragments formed by resolvase cleavage, for example by gel electrophoresis, indicates the presence of a mutation. Benefits of the EMD method are a single protocol to identify point mutations, deletions, and insertions assayed directly from PCR reactions eliminating the need for sample purification, shortening the hybridization time, and increasing the signal-to-noise ratio. Mixed samples containing up to a 20-fold excess of normal DNA and fragments up to 4 kb in size can been assayed. However, EMD scanning does not identify particular base changes that occur in mutation positive samples requiring additional sequencing procedures to identity of the mutation if necessary. CEL I enzyme can be used similarly to resolvase $T_4$ endonuclease VII as demonstrated in U.S. Pat. No. 5,869,245.

III. METHODS OF TREATMENT

Further provided herein are methods for treating or delaying progression of cancer in an individual comprising administering to the individual an effective amount of a CDK inhibitor, SAC component inhibitor, or a structurally similar inhibitor, to a subject determined to have an EGFR activating mutation, such as a L858R mutation, exon 20 deletion, and/or exon 20 insertion. The subject may have more than one EGFR activating mutation.

Examples of cancers contemplated for treatment include lung cancer, head and neck cancer, breast cancer, pancreatic cancer, prostate cancer, renal cancer, bone cancer, testicular cancer, cervical cancer, gastrointestinal cancer, lymphomas, pre-neoplastic lesions in the lung, colon cancer, melanoma, and bladder cancer. In particular aspects, the cancer is non-small cell lung cancer.

In some embodiments, the subject is a mammal, e.g., a primate, preferably a higher primate, e.g., a human (e.g., a patient having, or at risk of having, a disorder described herein). In one embodiment, the subject is in need of enhancing an immune response. In certain embodiments, the subject is, or is at risk of being, immunocompromised. For example, the subject is undergoing or has undergone a chemotherapeutic treatment and/or radiation therapy. Alternatively, or in combination, the subject is, or is at risk of being, immunocompromised as a result of an infection.

CDK inhibitors may be a CDK2 inhibitor, CDK5 inhibitor, CDK1 inhibitor, or CDK 9 inhibitor. The CDK inhibitor may be the CDK inhibitor is dinaciclib (SCH727965), alvocidib (flavopiridol), roscovitine (seliciclib, CYC202), SNS-032 (BMS-387032), LY2857785, ADZ5438, BMS-265246, NU6027, LDC000067, wogonin, or RO-3306. Additional exemplary CDK inhibitors include MSC2530818, senexin A, LDC4297 (LDC044297), PHA-793887, BS-181 HCl, PHA-767491, THZ1 2HCl, or XL413. In particular aspects, the CDK inhibitor may be dinaciclib or alvocidib.

SAC component inhibitors may be a polo-like kinase 1 (PLK1) inhibitor, Aurora kinase inhibitor, survivin, and/or KSP inhibitor. The PLK1 inhibitor may be BI 2536, volasertib, GSK461364, ON-01910, GW 843682X, or HMN-214. The Aurora kinase inhibitor may be a Pan-Aurora inhibitor, Aurora A/B inhibitor, or an Aurora A inhibitor. The Aurora kinase inhibitor may be AMG 900, alisertib, PF-03814735, Tozasertib, MLN8054, or SNS-314 Mesylate. The KSP inhibitor may be ispinesib or SB743921. The survivin inhibitor may be YM155. In some aspects, the SAC component inhibitor is not a MAD2 inhibitor.

Certain embodiments concern the administration of a TKI in combination with the CDK inhibitor and/or SAC component inhibitor. The TKI may be osimertinib, erlotinib, gefitinib, afatinib, poziotinib, dacomitinib, and CO-1686 or other TKIs known in the art. In some aspects, the TKI is poziotinib (also known as HM781-36B, HM781-36, and 1-[4-[4-(3,4-dichloro-2-fluoroanilino)-7-methoxyquinazolin-6-yl]oxypiperidin-1-yl]prop-2-en-1-one) is administered. Poziotinib is a quinazoline-based pan-HER inhibitor that irreversibly blocks signaling through the HER family of tyrosine-kinase receptors including HER1, HER2, and HER4. Poziotinib or structurally similar compounds (e.g., U.S. Pat. No. 8,188,102 and U.S. Patent Publication No. 20130071452; incorporated herein by reference) may be used in the present methods.

A. Pharmaceutical Compositions

Also provided herein are pharmaceutical compositions and formulations comprising a CDK inhibitor and/or a SAC component inhibitor, and a pharmaceutically acceptable carrier for subjects determined to have an EGFR activating mutation, such as a L858 mutation, exon 19 deletion, or exon 20 insertion.

Pharmaceutical compositions and formulations as described herein can be prepared by mixing the active ingredients (such as an antibody or a polypeptide) having the desired degree of purity with one or more optional pharmaceutically acceptable carriers (Remington's Pharmaceutical Sciences 22$^{nd}$ edition, 2012), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in U.S. Patent Publication Nos. 2005/0260186 and 2006/0104968. In one aspect, a sHASEGP is combined with one or more additional glycosaminoglycanases such as chondroitinases.

B. Combination Therapies

In certain embodiments, the compositions and methods of the present embodiments involve CDK inhibition and/or SAC component inhibition in combination with at least one additional therapy. The additional therapy may be radiation therapy, surgery (e.g., lumpectomy and a mastectomy), chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy.

In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy is therapy targeting PBK/AKT/mTOR pathway, HSP90 inhibitor, tubulin inhibitor, apoptosis inhibitor, and/or chemopreventative agent. The additional therapy may be one or more of the chemotherapeutic agents known in the art.

The inhibitors may be administered before, during, after, or in various combinations relative to an additional cancer therapy, such as immune checkpoint therapy. The administrations may be in intervals ranging from concurrently to minutes to days to weeks. In embodiments where the inhibitors is provided to a patient separately from an additional therapeutic agent, one would generally ensure that a significant period of time did not expire between the time of each delivery, such that the two compounds would still be able to exert an advantageously combined effect on the patient. In such instances, it is contemplated that one may provide a patient with the antibody therapy and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

Various combinations may be employed. For the example below a CDK inhibitor and/or SAC component inhibitor is "A" and an anti-cancer therapy is "B":

| | | | | | |
|---|---|---|---|---|---|
| A/B/A | B/A/B B/B/A | A/A/B | A/B/B B/A/A | A/B/B/B | B/A/B/B |
| B/B/B/A | B/B/A/B | A/A/B/B | A/B/A/B | A/B/B/A | B/B/A/A |
| B/A/B/A | B/A/A/B | A/A/A/B | B/A/A/A | A/B/A/A | A/A/B/A |

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

1. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammall and calicheamicin omegal1); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PS Kpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

2. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

3. Immunotherapy

The skilled artisan will understand that additional immunotherapies may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve as a targeting agent. Alternatively, the effector may be a lymphocyte carrying a surface molecule that interacts, either directly or indirectly, with a tumor cell target. Various effector cells include cytotoxic T cells and NK cells Antibody-drug conjugates have emerged as a breakthrough approach to the development of cancer therapeutics. Cancer is one of the leading causes of deaths in the world. Antibody-drug conjugates (ADCs) comprise monoclonal antibodies (MAbs) that are covalently linked to cell-killing drugs. This approach combines the high specificity of MAbs against their antigen targets with highly potent cytotoxic drugs, resulting in "armed" MAbs that deliver the payload (drug) to tumor cells with enriched levels of the antigen.

Targeted delivery of the drug also minimizes its exposure in normal tissues, resulting in decreased toxicity and improved therapeutic index. The approval of two ADC drugs, ADCETRIS® (brentuximab vedotin) in 2011 and KADCYLA® (trastuzumab emtansine or T-DM1) in 2013 by FDA validated the approach. There are currently more than 30 ADC drug candidates in various stages of clinical trials for cancer treatment (Leal et al., 2014). As antibody engineering and linker-payload optimization are becoming more and more mature, the discovery and development of new ADCs are increasingly dependent on the identification and validation of new targets that are suitable to this approach and the generation of targeting MAbs. Two criteria for ADC targets are upregulated/high levels of expression in tumor cells and robust internalization. p In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies include immune adjuvants, e.g., *Mycobacterium bovis, Plasmodium falciparum,* dinitrochlorobenzene, and aromatic compounds (U.S. Pat. Nos. 5,801,005 and 5,739,169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Patent 5,824,311). It is contemplated that one or more anti-cancer therapies may be employed with the antibody therapies described herein.

In some embodiments, the immunotherapy may be an immune checkpoint inhibitor. Immune checkpoints either turn up a signal (e.g., co-stimulatory molecules) or turn down a signal. Inhibitory immune checkpoints that may be targeted by immune checkpoint blockade include adenosine A2A receptor (A2AR), B7-H3 (also known as CD276), B and T lymphocyte attenuator (BTLA), cytotoxic T-lymphocyte-associated protein 4 (CTLA-4, also known as CD152), indoleamine 2,3-dioxygenase (IDO), killer-cell immunoglobulin (KIR), lymphocyte activation gene-3 (LAGS), programmed death 1 (PD-1), T-cell immunoglobulin domain and mucin domain 3 (TIM-3) and V-domain Ig suppressor of T cell activation (VISTA). In particular, the immune checkpoint inhibitors target the PD-1 axis and/or CTLA-4.

The immune checkpoint inhibitors may be drugs such as small molecules, recombinant forms of ligand or receptors, or, in particular, are antibodies, such as human antibodies (e.g., International Patent Publication WO2015016718; Pardoll, *Nat Rev Cancer,* 12(4): 252-64, 2012; both incorporated herein by reference). Known inhibitors of the immune checkpoint proteins or analogs thereof may be used, in particular chimerized, humanized or human forms of antibodies may be used. As the skilled person will know, alternative and/or equivalent names may be in use for certain antibodies mentioned in the present disclosure. Such alternative and/or equivalent names are interchangeable in the context of the present invention. For example it is known that lambrolizumab is also known under the alternative and equivalent names MK-3475 and pembrolizumab.

In some embodiments, the PD-1 binding antagonist is a molecule that inhibits the binding of PD-1 to its ligand binding partners. In a specific aspect, the PD-1 ligand binding partners are PDL1 and/or PDL2. In another embodiment, a PDL1 binding antagonist is a molecule that inhibits the binding of PDL1 to its binding partners. In a specific aspect, PDL1 binding partners are PD-1 and/or B7-1. In another embodiment, the PDL2 binding antagonist is a molecule that inhibits the binding of PDL2 to its binding partners. In a specific aspect, a PDL2 binding partner is PD-1. The antagonist may be an antibody, an antigen binding fragment thereof, an immunoadhesin, a fusion protein, or oligopeptide. Exemplary antibodies are described in U.S. Pat. Nos. 8,735,553, 8,354,509, and 8,008,449, all incorporated herein by reference. Other PD-1 axis antagonists for use in the methods provided herein are known in the art such as described in U.S. Patent Publication Nos. US20140294898, US2014022021, and US20110008369, all incorporated herein by reference.

In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the PD-1 binding antagonist is AMP-224. Nivolumab, also known as MDX-1106-04, MDX-1106, ONO-4538, BMS-936558, and OPDIVO®, is an anti-PD-1 antibody described in W02006/121168. Pembrolizumab, also known as MK-3475, Merck 3475, lambrolizumab, KEYTRUDA®, and SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PDL2-Fc fusion soluble receptor described in WO2010/027827 and WO2011/066342.

Another immune checkpoint that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off" switch when bound to CD80 or CD86 on the surface of antigen-presenting cells. CTLA4 is a member of the immunoglobulin superfamily that is expressed on the surface of Helper T cells and transmits an inhibitory signal to T cells. CTLA4 is similar to the T-cell co-stimulatory protein, CD28, and both molecules bind to CD80 and CD86, also called B7-1 and B7-2 respectively, on antigen-presenting cells. CTLA4 transmits an inhibitory signal to T cells, whereas CD28 transmits a stimulatory signal. Intracellular CTLA4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide.

Anti-human-CTLA-4 antibodies (or VH and/or VL domains derived therefrom) suitable for use in the present methods can be generated using methods well known in the art. Alternatively, art recognized anti-CTLA-4 antibodies can be used. For example, the anti-CTLA-4 antibodies disclosed in: U.S. Patent No. 8,119,129; International Patent Publication Nos. WO 01/14424, WO 98/42752, and WO 00/37504 (CP675,206, also known as tremelimumab; formerly ticilimumab); U.S. Pat. No. 6,207,156; Hurwitz et al., 1998; Camacho et al., 2004; and Mokyr et al., 1998 can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Application Nos. WO2001014424, and WO2000037504, and U.S. Pat. No. 8,017,114; all incorporated herein by reference.

An exemplary anti-CTLA-4 antibody is ipilimumab (also known as 10D1, MDX-010, MDX-101, and Yervoy®) or antigen binding fragments and variants thereof (see, e.g., WO 01/14424). In other embodiments, the antibody comprises the heavy and light chain CDRs or VRs of ipilimumab. Accordingly, in one embodiment, the antibody comprises the CDR1, CDR2, and CDR3 domains of the VH region of ipilimumab, and the CDR1, CDR2 and CDR3 domains of the VL region of ipilimumab. In another embodiment, the antibody competes for binding with and/or binds to the same epitope on CTLA-4 as the above-mentioned antibodies. In another embodiment, the antibody has at least about 90% variable region amino acid sequence identity with the above-mentioned antibodies (e.g., at least about 90%, 95%, or 99% variable region identity with ipilimumab).

Other molecules for modulating CTLA-4 include CTLA-4 ligands and receptors such as described in U.S. Pat. Nos. 5,844,905, 5,885,796 and International Patent Application Nos. WO1995001994 and WO1998042752; all incorporated herein by reference, and immunoadhesins such as described in U.S. Pat. No. 8,329,867, incorporated herein by reference.

4. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

IV. KIT

Also within the scope of the present disclosure are kits for detecting EGFR activating mutations, such as those disclosed herein. An example of such a kit may include a set of L858R, exon 19 deletion, and/or exon 20 mutation-specific primer. The kit may further comprise instructions for use of the primers to detect the presence or absence of the specific EFGR activating mutations described herein. The kit may further comprise instructions for diagnostic purposes, indicating that a positive identification of EGFR activating mutations described herein in a sample from a cancer patient indicates sensitivity to the CDK inhibitor and/or SAC component inhibitor. The kit may further comprise instructions that indicate that a positive identification of EGFR activating mutations described herein in a sample from a cancer patient indicates that a patient should be treated with a CDK inhibitor and/or SAC component inhibitor.

V. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Identification of Methods for Treating Cancers With EGFR Activating Mutations While EGFR mutant NSCLC patients are initially responsive to EGFR targeted therapies, resistant disease inevitably emerges and in nearly half of resistance cases, tumors lack secondary EGFR mutations such as T790M and are refractory to 2nd and 3rd generation EGFR tyrosine kinase inhibitors (TKI). The identification of treatment regimens with efficacy against T790M-negative resistance remains a major clinical challenge. To address this unmet need, a panel of NSCLC cell lines with acquired resistance to the EGFR TKI, erlotinib, gefitinib, osimertinib or poziotinib were derived.

Proteomic profiling of resistant cells was performed by reverse phase protein array (RPPA) and Western blotting for markers of epithelial to mesenchymal transition (EMT). Cell Titer glow assay in a high-throughput 384 well plate system was utilized for drug screening. Long-term effect of SAC and CDK inhibitors was evaluated by J 4 day clonogenic assay.

Using HCC827 and HCC4006 (EGFR mutant NSCLC cells), EGFR TKI resistant variants were derived in vitro by continuously culturing cells in increasing concentrations of the TKI, such as erlotinib. Erlotinib resistant cells (ER) were negative for secondary EGFR mutations and were resistant to 2nd and 3rd generation EGFR TKIs including osimertinib, afatinib, and dacomitinib (FIG. 1) and had undergone epithelial to mesenchymal transition (EMT) as demonstrated by loss of E-cadherin, enhanced expression of N-cadherin and Axl and an increased invasive phenotype as determined by Boyden chamber assay. Proteomic profiling revealed that although EGFR TKI resistant cells displayed similar mesenchymal and invasive phenotypes, there was significant heterogeneity in protein expression and pathway activation among resistant variants derived from the same parental cell line.

To identify therapeutic agents with activity against EMT-associated EGFR TKI resistance, a high-throughput drug screening was performed to test the efficacy of 1,321 compounds. EMT-associated EGFR TKI resistance was accompanied by the acquisition of broad-spectrum drug resistance. Compared to parental cells, mesenchymal EGFR TKI resistant cells were significantly more resistant to chemotherapeutic agents used to treat NSCLC including pemetrexed, irinotecan, vinblastine, and gemcitabine. EGFR TKI resistant cells displayed acquired resistance to 147 other tyrosine kinase and serine/threonine kinase inhibitors. In contrast, both parental cells and mesenchymal EGFR TKI resistant variants were highly sensitive to CDK inhibitors and agents targeting spindle assembly checkpoint (SAC) components including PLK1, Aurora, KSP, and survivin. These finding were validated by MTS and clonogenic assays. Treatment with SAC inhibitors induced the accumulation of cells in G2/M phase, enlarged nuclear size, and polyploidy.

To clinically validate these findings, a cell line (MDA-011) was established from the pleural effusion of an EGFR mutant NSCLC patient with T790M-negative resistance to erlotinib. In vitro, MDA-011 cells were resistant to erlotinib and osimertinib. MDA-011 cells were highly sensitive to CDK inhibitors and SAC inhibitors as determined by MTS and clonogenic assays. These data indicated that EMT-associated resistance to EGFR TKIs is associated with broad spectrum drug resistance but have vulnerabilities to CDK and SAC inhibition which can be exploited to overcome resistant disease in NSCLC patients.

TABLE 1

IC50 for SAC inhibitor for 5 day Cell Titer Glo Assay.

| Drug | Target | HCC4006 $GIC_{50}$ (μM) | HCC4006 ER $GIC_{50}$ (μM) |
|---|---|---|---|
| BI 2538 | PLK1 | 0.01 | 0.01 |
| BI6727 (Volasertib) | PLK1 | 0.01 | 0.01 |
| GSK461364 | PLK1 | 0.01 | 0.01 |
| ON-01910 | PLK1 | 0.02 | 0.02 |

TABLE 1-continued

IC50 for SAC inhibitor for 5 day Cell Titer Glo Assay.

| Drug | Target | HCC4006 $GIC_{50}$ (μM) | HCC4006 ER $GIC_{50}$ (μM) |
|---|---|---|---|
| GW 843682X | PLK1 | 0.32 | 0.30 |
| HMN-214 | PLK1 | 0.55 | 0.64 |
| AMG 900 | Pan-Aurora | 0.01 | 0.01 |
| MLN8237 (Alisertib) | Aurora A | 0.02 | 0.02 |
| PF-03814735 | Aurora A/B | 0.02 | 0.02 |
| TOZASERTIB | Aurora A | 0.05 | 0.06 |
| MLN8054 | Pan-Aurora | 0.16 | 0.18 |
| SNS-314 Mesylate | Pan-Aurora | 0.01 | 0.01 |
| Ispinesib | KSP | 0.01 | 0.01 |
| SB 743921 | KSP | 0.01 | 0.01 |
| YM155 | Survivin | 0.01 | 0.01 |

TABLE 2

IC50 for SAC inhibitor for 5 day Cell Titer Glo Assay.

| Drug | Target | HCC4006 $GIC_{50}$ (μM) | HCC4006 ER $GIC_{50}$ (μM) |
|---|---|---|---|
| BI 2538 | PLK1 | 0.01 | 0.07 |
| BI6727 (Volasertib) | PLK1 | 0.01 | 0.54 |
| GSK461364 | PLK1 | 0.01 | 0.01 |
| ON-01910 | PLK1 | 0.02 | 0.02 |
| GW 843682X | PLK1 | 0.17 | 0.22 |
| HMN-214 | PLK1 | 0.70 | 0.69 |
| ON-01910 | PLK1 | 0.01 | 0.02 |
| AMG 900 | Pan-Aurora | 0.01 | 0.01 |
| MLN8054 | Pan-Aurora | 0.25 | 0.08 |
| MLN8237 (Alisertib) | Aurora A | 0.03 | 0.02 |
| PF-03814735 | Aurora A/B | 0.02 | 0.02 |
| SNS-314 Mesylate | Pan-Aurora | 0.05 | 0.03 |
| TOZASERTIB | Aurora A | 0.02 | 0.04 |
| Ispinesib (SB-713992) | KSP | 0.01 | 0.03 |
| SB 743921 | KSP | 0.01 | 0.03 |
| YM155 | Survivin | 0.01 | 0.03 |

TABLE 3

IC50 for CDK inhibitor for 5 day Cell Titer Glow Assay.

| Drug | Target | HCC4006 $GIC_{50}$ (μM) | HCC4006 ER $GIC_{50}$ (μM) |
|---|---|---|---|
| AZD5438 | CDK | 0.18 | 0.28 |
| Dinaciclib | CDK | 0.01 | 0.01 |
| Alvocidib | CDK | 0.05 | 0.04 |
| Abemaciclib | CDK | 0.03 | 0.30 |
| Pelbociclib | CDK | 0.04 | 0.04 |
| AZD5438 | CDK | 0.16 | 0.11 |
| Dinaciclib | CDK | 0.01 | 0.01 |
| Alvocidib | CDK | 0.03 | 0.03 |
| Abemaciclib | CDK | 0.06 | 0.11 |
| Pelbociclib | CDK | 0.40 | 0.88 |

Figure 7:
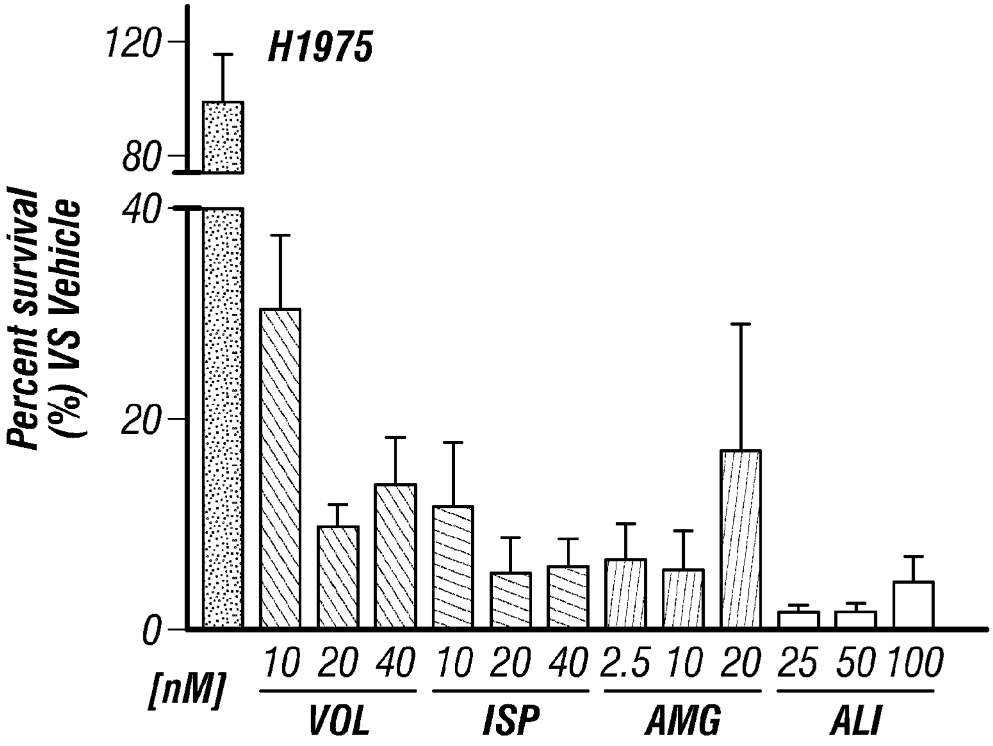
FIG. 7: EGFR mutant H1975 cells are highly sensitive to the EGFR inhibitor osimertinib. H.1975 cells were cultured continuously in osimertinib until resistant cells emerged (H1975 ORS and H1975 OR16). Both parental H1975 and H1975 ORS and H1975 OR16 (osimertinib resistant) cells were sensitive to SAC inhibitors including drugs targeting PLK1 (volasertib), KSP (ispinasib) and aurora kinases (AMG900 and Alisertib).
Figure 7:
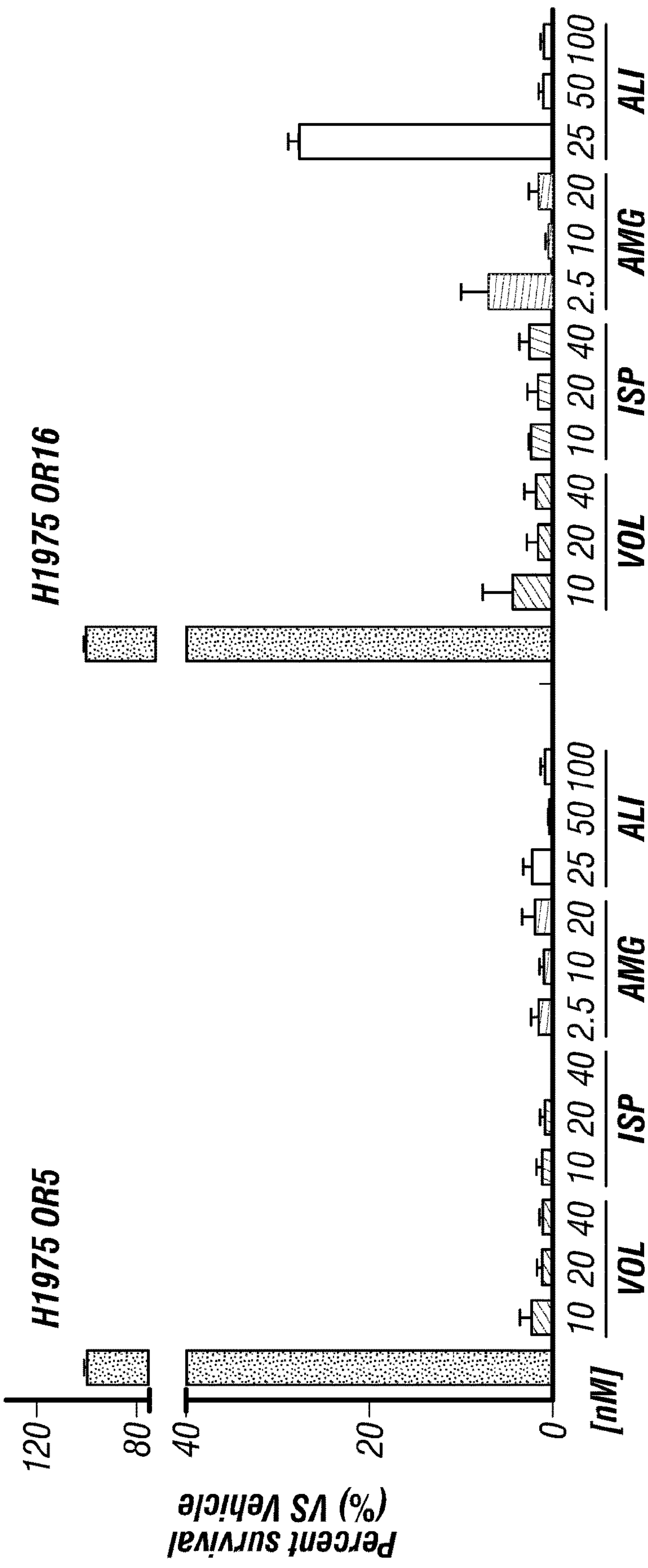

Next, H1975 cells (EGFR mutation positive with T790M) were cultured in osimertinib until resistant variants emerged. Osimertinib resistant cells (H1975 OR5 and H1975 OR16) had undergone EMT and were sensitive to CDK inhibitors and agents targeting SAC components including PLKI (volasertib), Aurora (AMG-900 and alisertib), KSP (ispinesib) (FIG. 7).

In addition, the CDK and SAC inhibitors were investigated in the setting of acquired resistance to inhibitors with activity against EGFR exon 20 insertion mutations. YUL-0019 cells harbor an EGFR exon 20 insertion mutation and are highly sensitive to the EGFR inhibitor, poziotinib. YUL-0019 cells were continuously cultured in poziotinib until resistant cells emerged. YUL-0019 cells and YUL-0019 PR8

Figure 8:
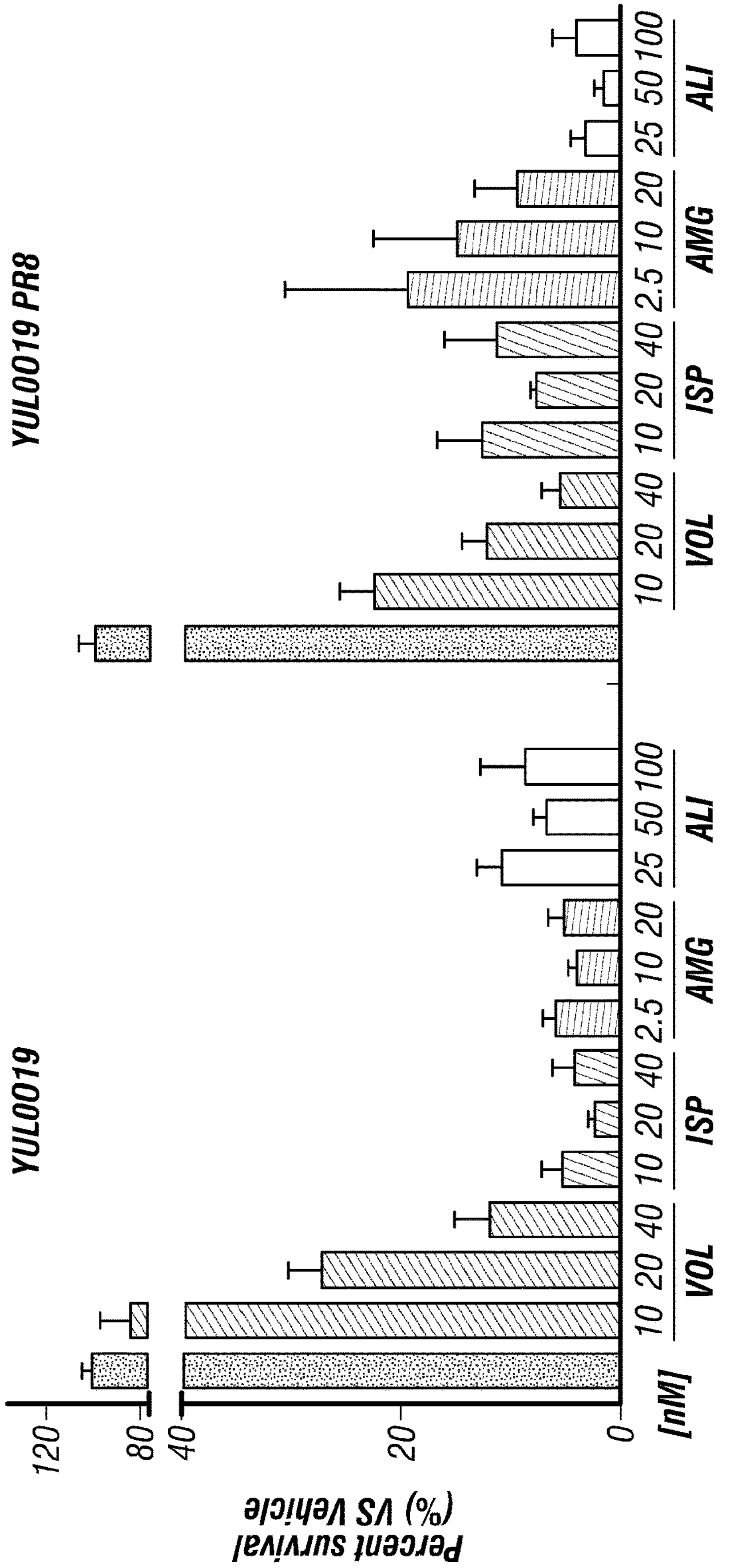
FIG. 8: YUL0019 cells which harbor an EGFR exon 20 insertion mutation are highly sensitive to the EGFR inhibitor poziotinib. YUL0019 cells were cultured continuously in poziotinib until resistant cells emerged (YUL0019 PR8). Both parental YUL0019 and YUL0019 PR8 (poziotinib resistant) cells were sensitive to SAC inhibitors including drugs targeting PLK1 (volasertib), KSP (ispinasib) and aurora kinases (AMG900 and Alisertib).

(poziotinib resistant) cells were highly sensitive to CDK inhibitors (including dinaciclib and alvocidib) SAC inhibitors including PLKI (volasertib), Aurora (AMG-900 and alisertib), and KSP (ispinesib) (FIG. 8). These data indicate that EMT-associated resistance to EGFR TKIs is associated with broad spectrum drug resistance but have vulnerabilities to CDK and SAC inhibition which can be exploited to overcome resistant disease in NSCLC patients.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Austin-Ward and Villaseca, *Revista Medica de Chile,* 126 (7):838-845, 1998.
Ausubel et al., Current Protocols in Molecular Biology, John Wiley & Sons, New York, N.Y., 2003.
Bukowski et al., *Clinical Cancer Res.,* 4(10):2337-2347, 1998.
Camacho et al. *J Clin Oncology* 22(145): Abstract No. 2505 (antibody CP-675206), 2004.
Chee et al., *Science,* 274:610-614, 1996.
Cho et al., *Cancer Res* 73:6770-9, 2013.
Christodoulides et al., *Microbiology,* 144(Pt 11):3027-3037, 1998.
Church and Gilbert, *Proc. Natl. Acad. Sci. USA* 81:1991-1995 (1988).
Cotton etal., *Proc. Natl. Acad. Sci. USA* 85:4397-4401 (1985).
Davidson et al., *J. Immunother.,* 21(5):389-398, 1998.
Del Tito et al., *Clinical Chemistry* 44:731-739, 1998.
Drmanac et al., *Nat. Biotechnol.,* 16:54-58, 1998.
Drmanac et al., *Science,* 260:1649-1652, 1993.
Flavell et. al., *Cell* 15:25 (1978).
Fu et al., *Nat. Biotechnol.,* 16:381-384, 1998/
Geever et al., *Proc. Natl. Acad. Sci. USA* 78:5081 (1981).
Hanibuchi et al., *Int. J. Cancer,* 78(4):480-485, 1998.
Hellstrand et al., *Acta Oncologica,* 37(4):347-353, 1998.
Hollander, *Front. Immun.,* 3:3, 2012.
Hui and Hashimoto, *Infection Immun.,* 66(11):5329-5336, 1998.
Hurwitz et al. *Proc Natl Acad Sci USA* 95(17): 10067-10071, 1998.
International Patent Publication No. WO 99/57318
International Patent Publication No. WO1995001994
International Patent Publication No. WO1998042752
International Patent Publication No. WO2000037504
International Patent Publication No. WO2001014424
International Patent Publication No. WO2009/101611
International Patent Publication No. WO2009/114335
International Patent Publication No. WO2010/027827
International Patent Publication No. WO2011/066342
International Patent Publication No. WO2015016718
International Patent Publication No. WO01/14424
International Patent Publication No. WO98/42752
Leal, M., *Ann NY Acad Sci* 1321, 41-54, 2014.
Mokyr et al. *Cancer Res* 58:5301-5304, 1998.
Pardoll, *Nat Rev Cancer,* 12(4): 252-64, 2012.
Qin et al., *Proc. Natl. Acad. Sci. USA,* 95(24):14411-14416, 1998.
Raca et al., *Genet Test* 8(4):387-94 (2004).
Sanger et al., *Proc. Natl. Acad. Sci. USA* 74:5463-5467 (1977).
Sears et al., *Biotechniques,* 13:626-633, 1992.
Sheffield et al., *Proc. Natl. Acad. Sci. USA* 86:232-236 (1989).
U.S. Pat. No. 4,870,287
U.S. Pat. No. 5,288,644
U.S. Pat. No. 5,739,169
U.S. Pat. No. 5,760,395
U.S. Pat. No. 5,801,005
U.S. Pat. No. 5,824,311
U.S. Pat. No. 5,830,880
U.S. Pat. No. 5,844,905
U.S. Pat. No. 5,846,945
U.S. Pat. No. 5,869,245
U.S. Pat. No. 5,885,796
U.S. Pat. No. 6,207,156
U.S. Pat. No. 8,008,449
U.S. Pat. No. 8,017,114
U.S. Pat. No. 8,119,129
U.S. Pat. No. 8,188,102
U.S. Pat. No. 8,329,867
U.S. Pat. No. 8,354,509
U.S. Pat. No. 8,735,553
U.S. Patent Publication No. 2004/0014095
U.S. Patent Publication No. 2005/0260186
U.S. Patent Publication No. 2006/0104968
U.S. Patent Publication No. 20110008369
U.S. Patent Publication No. 20130071452
U.S. Patent Publication No. 2014022021
U.S. Patent Publication No. 20140294898
Zimmerman et al., *Methods Mol. Cell. Biol.,* 3:39-42, 1992.

The invention claimed is:

1. A method of treating non-small cell lung cancer (NSCLC) in a subject comprising administering an effective amount of a cyclin dependent kinase (CDK) inhibitor to the subject, wherein the NSCLC is determined to have one or more EGFR activating mutations selected from the group consisting of an E746-A750 deletion, L747-E749 deletion, A750P, and N771Del Ins FH, is resistant to one or more tyrosine kinase inhibitors (TKIs), and has undergone epithelial to mesenchymal transition (EMT) and wherein the subject is determined to not have a T790M mutation and the CDK inhibitor is a CDK2 inhibitor, CDK5 inhibitor, CDK1 inhibitor, and/or CDK9 inhibitor.

2. The method of claim 1, wherein the cancer is determined to further comprise a L858R mutation, or an exon 20 insertion.

3. The method of claim 1, wherein the CDK inhibitor is dinaciclib (SCH727965), alvocidib (flavopiridol), roscovitine (seliciclib, CYC202), SNS-032 (BMS-387032), LY2857785, ADZ5438, BMS-265246, NU6027, LDC000067, wogonin, or RO-3306.

4. The method of claim 1, wherein EMT is demonstrated by decreased E-cadherin expression, increased expression of vimentin and/or Axl, and/or an increased invasive phenotype.

5. The method of claim 1, wherein the subject is further determined to comprise a secondary mutation comprising C797S resistance mutation or L792H resistance mutation.

6. The method of claim 1, further comprising administering a TKI and/or chemotherapy.

* * * * *